(12) United States Patent
Kim

(10) Patent No.: US 7,459,602 B2
(45) Date of Patent: *Dec. 2, 2008

(54) MAMMALIAN CANCER CELL AND TRANSGENIC MAMMAL CARRYING HUMAN PROTOONCOGENE AND KIT FOR DIAGNOSING CANCER USING SAID PROTOONCOGENE

(76) Inventor: Jin-Woo Kim, Hyundai Apt. 118-804, Apkujung-dong, Kangnam-ku, Seoul (KR) 135-110

( * ) Notice: Subject to any disclaimer, the term of this patent is extended or adjusted under 35 U.S.C. 154(b) by 399 days.

This patent is subject to a terminal disclaimer.

(21) Appl. No.: 10/465,950

(22) PCT Filed: Jul. 11, 2001

(86) PCT No.: PCT/KR01/01187

§ 371 (c)(1),
(2), (4) Date: Jun. 26, 2003

(87) PCT Pub. No.: WO02/053710

PCT Pub. Date: Jul. 11, 2002

(65) Prior Publication Data

US 2004/0111758 A1  Jun. 10, 2004

(30) Foreign Application Priority Data

Jan. 2, 2001  (KR) ............... 10-2001-0000041

(51) Int. Cl.
*A01K 67/00* (2006.01)
(52) U.S. Cl. ............ 800/18; 800/8; 800/9; 800/10; 800/13; 424/93.2; 424/93.21
(58) Field of Classification Search .......... None
See application file for complete search history.

(56) References Cited

U.S. PATENT DOCUMENTS 6,815,180 B1 * 11/2004 Kim .................. 435/69.1
6,905,844 B2 * 6/2005 Kim .................. 435/69.1
6,977,296 B2 * 12/2005 Kim .................. 536/23.5

OTHER PUBLICATIONS

Nebert et al, Biochemical Pharmacol Feb. 1997;53:249-54.*
Hammer et al, J Anim Sci 1986;63:269-78.*
Mullins et al, J Clin Invest Apr. 1996;97:1557-60.*
Wall et al, J Dairy Sci 1997;80:2213-24.*
Pearson, Nature 2002;415:8-9.*
Linder, Lab Animal May 2001;30:34-9.*
Logan and Sharma, Clin Exp Pharmacol Physiol Dec. 1999;26:1020-25.*

* cited by examiner

*Primary Examiner*—Q. Janice Li
(74) *Attorney, Agent, or Firm*—Baker & Hostetler, LLP

(57) ABSTRACT

The present invention provides a mammalian cell transfected with an expression vector comprising a human protooncogene which has the nucleotide sequence of SEQ ID NO: 1; a mammalian embryo carrying a nucleic acid construct comprising the human protooncogene; a transgenic cancer mammal, which is derived from the mammalian embryo; and a kit for diagnosing a cancer selected from the group consisting of breast, kidney, ovary and stomach cancers, which comprises a probe having the nucleotide sequence complementary to mRNA transcribed from the human protooncogene or a portion of the mRNA; or an antibody binding specifically to a protein translated from the mRNA or a portion of the protein.

9 Claims, 25 Drawing Sheets

IP: anti-FLAG kD    1    2

83 —
50.7 —
35.7 —

Blot: anti-GST

IP: anti-GST kD    1    2

83 —
50.7 —
35.7 — anti-FLAG

SEQUENCE LISTING

<160> NUMBER OF SEQ ID NOS: 5

<210> SEQ ID NO 1
<211> LENGTH: 2118
<212> TYPE: DNA
<213> ORGANISM: Homo sapiens
<220> FEATURE:
<221> NAME/KEY: CDS
<222> LOCATION: (9)..(1088)
<220> FEATURE:
<221> NAME/KEY: sig_peptide
<222> LOCATION: (9)..(83)
<220> FEATURE:
<221> NAME/KEY: misc_feature
<222> LOCATION: (435)..(494)
<223> OTHER INFORMATION: transmembrane domain

<400> SEQUENCE: 1

```
ctgtgaag  atg gcg ctc tcc agg gtg tgc tgg gct cgg tcg gct gtg tgg    50
          Met Ala Leu Ser Arg Val Cys Trp Ala Arg Ser Ala Val Trp
          1               5                   10
```

| | | |
|---|---|---|
| ggc tcg gca gtc acc cct gga cat ttt gtc acc cgg agg ctg caa ctt<br>Gly Ser Ala Val Thr Pro Gly His Phe Val Thr Arg Arg Leu Gln Leu<br>15                    20                   25               30 | | 98 |
| ggt cgc tct ggc ctg gct tgg ggg gcc cct cgg tct tca aag ctt cac<br>Gly Arg Ser Gly Leu Ala Trp Gly Ala Pro Arg Ser Ser Lys Leu His<br>               35                   40                   45 | | 146 |
| ctt tct cca aag gca gat gtg aag aac ttg atg tct tat gtg gta acc<br>Leu Ser Pro Lys Ala Asp Val Lys Asn Leu Met Ser Tyr Val Val Thr<br>          50                   55                   60 | | 194 |
| aag aca aaa gcg att aat ggg aaa tac cat cgt ttc ttg ggt cgt cat<br>Lys Thr Lys Ala Ile Asn Gly Lys Tyr His Arg Phe Leu Gly Arg His<br>65                    70                   75 | | 242 |
| ttc ccc cgc ttc tat atc ctg tac aca atc ttc atg aaa gga ttg cag<br>Phe Pro Arg Phe Tyr Ile Leu Tyr Thr Ile Phe Met Lys Gly Leu Gln<br>          80                   85                   90 | | 290 |
| atg tta tgg gct gat gcc aaa aag gct aga aga ata aag aca aat atg<br>Met Leu Trp Ala Asp Ala Lys Lys Ala Arg Arg Ile Lys Thr Asn Met<br>95                    100                105               110 | | 338 |
| tgg aag cac aat ata aag ttt cat caa ctt cca tac cgg gag atg gag<br>Trp Lys His Asn Ile Lys Phe His Gln Leu Pro Tyr Arg Glu Met Glu<br>                115                120               125 | | 386 |
| cat ttg aga cag ttc cgc caa gac gtc acc aag tgt ctt ttc cta ggt<br>His Leu Arg Gln Phe Arg Gln Asp Val Thr Lys Cys Leu Phe Leu Gly<br>                130                135               140 | | 434 |
| att att tcc att cca cct ttt gcc aac tac ctg gtc ttc ttg cta atg<br>Ile Ile Ser Ile Pro Pro Phe Ala Asn Tyr Leu Val Phe Leu Leu Met<br>                145                150               155 | | 482 |
| tac ctg ttt ccc agg caa cta ctg atc agg cat ttc tgg acc cca aaa<br>Tyr Leu Phe Pro Arg Gln Leu Leu Ile Arg His Phe Trp Thr Pro Lys<br>                160                165               170 | | 530 |
| caa caa act gat ttc tta gat atc tat cat gct ttc cgg aag cag tcc<br>Gln Gln Thr Asp Phe Leu Asp Ile Tyr His Ala Phe Arg Lys Gln Ser<br>175                  180                185               190 | | 578 |
| cac cca gaa att att agt tat tta gaa aag gtc atc cct ctc att tct<br>His Pro Glu Ile Ile Ser Tyr Leu Glu Lys Val Ile Pro Leu Ile Ser<br>                195                200               205 | | 626 |
| gat gca gga ctc cgg tgg cgt ctg aca gat ctg tgc acc aag ata cag<br>Asp Ala Gly Leu Arg Trp Arg Leu Thr Asp Leu Cys Thr Lys Ile Gln<br>                210                215               220 | | 674 |
| cgt ggt acc cac cca gca ata cat gat atc ttg gct ctg aga gag tgt<br>Arg Gly Thr His Pro Ala Ile His Asp Ile Leu Ala Leu Arg Glu Cys<br>                225                230               235 | | 722 |
| ttc tct aac cat cct ctg ggc atg aac caa ctc cag gct ttg cac gtg<br>Phe Ser Asn His Pro Leu Gly Met Asn Gln Leu Gln Ala Leu His Val<br>                240                245               250 | | 770 |
| aaa gcc ttg agc cgg gcc atg ctt ctc aca tct tac ctg cct cct ccc<br>Lys Ala Leu Ser Arg Ala Met Leu Leu Thr Ser Tyr Leu Pro Pro Pro<br>255                  260                265               270 | | 818 |
| ttg ttg aga cat cgt ttg aag act cat aca act gtg att cac caa ctg<br>Leu Leu Arg His Arg Leu Lys Thr His Thr Thr Val Ile His Gln Leu<br>                275                280               285 | | 866 |
| gac aag gct ttg gca aag ctg ggg att ggc cag ctg act gct cag gaa<br>Asp Lys Ala Leu Ala Lys Leu Gly Ile Gly Gln Leu Thr Ala Gln Glu<br>                290                295               300 | | 914 |
| gta aaa tcg gct tgt tat ctc cgt ggc ctg aat tct acg cat att ggt<br>Val Lys Ser Ala Cys Tyr Leu Arg Gly Leu Asn Ser Thr His Ile Gly<br>                305                310               315 | | 962 |
| gaa gat agg tgt cga act tgg ctg gga gaa tgg ctg cag att tcc tgc<br>Glu Asp Arg Cys Arg Thr Trp Leu Gly Glu Trp Leu Gln Ile Ser Cys<br>320                  325                330 | | 1010 |

```
agc ctg aaa gaa gct gag ctg tct ctc ttg ctg cac aac gtg gtc ctg      1058
Ser Leu Lys Glu Ala Glu Leu Ser Leu Leu Leu His Asn Val Val Leu
335                 340                 345                 350 ctc tcc acc aac tac ctt ggg aca agg cgc tg  aatgaaccat ggagcggat     1110
Leu Ser Thr Asn Tyr Leu Gly Thr Arg Arg
                355                 360 gcattgtcct gcagtcgtat agtatagcag tgcaggaaca aacagcactt gccagcaaag    1170
tctgtgtgta ctgttaagtg tgtgggaggc agagagagga gcaggggcca tgggcttcac    1230
agcatggcac acctgtggga actgcagaca ttcctctcac agctagaact gaaacaaacc    1290
ctcttgctag gggtggtccg tgtgaggtgt catcctgtcc ccctcataat tactaatagc    1350
tggaactggc agcagcctct actgggcttt tactgtgatg tgttcagttc atgtcctagg    1410
aagtcagctt ttgccccagg tgggaatcct tatttggctt aggactgatc cacttccatg    1470
ttacttacat ctgtgggttt tgttgttgc tgttagaaaa ttttggctg gtgaaaacag      1530
cactcctttg gctggagcac ttgtgtccat gcatgtactt gggtgtttcc ctccatcctt    1590
tctgatatga ccaaaaatca gttgttttg ttttttgtca ccttcactgg catgggctaa     1650
ccacttcttt tcaaaccct ctgaacacct tttctgatg ggtaacttgc aggaatattc      1710
tattggaaaa gataacagga agtacaagtg cttcttgacc ccttcctcaa tgtttctagc    1770
cttcactctc cattgtcttt tctgggctgt attacagccc tctgtggatc ttcaactctg    1830
ctgcctccac tgtgatgcag cagtccaact gtaactgaca gtggctgcct tctctgggcc    1890
atggatcaca cctgtaaggt actaattact gcccagcctg gggagatcag gagaggtctg    1950
catagttagt aagttgggtt tagcttttgt gtgtgcatca gtgacttaga gttctgtaat    2010
aacttattgt aaatgcatga agcactgttt ttaaacccaa gtaaagactg cttgaaacct    2070
gttgatggaa aaaaaaaaaa aaaaaaaaaa aaaaaaaaaa aaaaaaaa                 2118
```

<210> SEQ ID NO 2
<211> LENGTH: 360
<212> TYPE: PRT
<213> ORGANISM: Homo sapiens

<400> SEQUENCE: 2

```
Met Ala Leu Ser Arg Val Cys Trp Ala Arg Ser Ala Val Trp Gly Ser
 1               5                  10                  15

Ala Val Thr Pro Gly His Phe Val Thr Arg Arg Leu Gln Leu Gly Arg
                20                  25                  30

Ser Gly Leu Ala Trp Gly Ala Pro Arg Ser Ser Lys Leu His Leu Ser
        35                  40                  45

Pro Lys Ala Asp Val Lys Asn Leu Met Ser Tyr Val Val Thr Lys Thr
    50                  55                  60

Lys Ala Ile Asn Gly Lys Tyr His Arg Phe Leu Gly Arg His Phe Pro
65                  70                  75                  80

Arg Phe Tyr Ile Leu Tyr Thr Ile Phe Met Lys Gly Leu Gln Met Leu
                85                  90                  95

Trp Ala Asp Ala Lys Lys Ala Arg Arg Ile Lys Thr Asn Met Trp Lys
                100                 105                 110

His Asn Ile Lys Phe His Gln Leu Pro Tyr Arg Glu Met Glu His Leu
        115                 120                 125

Arg Gln Phe Arg Gln Asp Val Thr Lys Cys Leu Phe Leu Gly Ile Ile
    130                 135                 140
```

```
Ser Ile Pro Pro Phe Ala Asn Tyr Leu Val Phe Leu Met Tyr Leu
145                 150                 155                 160

Phe Pro Arg Gln Leu Leu Ile Arg His Phe Trp Thr Pro Lys Gln Gln
            165                 170                 175

Thr Asp Phe Leu Asp Ile Tyr His Ala Phe Arg Lys Gln Ser His Pro
            180                 185                 190

Glu Ile Ile Ser Tyr Leu Glu Lys Val Ile Pro Leu Ile Ser Asp Ala
            195                 200                 205

Gly Leu Arg Trp Arg Leu Thr Asp Leu Cys Thr Lys Ile Gln Arg Gly
210                 215                 220

Thr His Pro Ala Ile His Asp Ile Leu Ala Leu Arg Glu Cys Phe Ser
225                 230                 235                 240

Asn His Pro Leu Gly Met Asn Gln Leu Gln Ala Leu His Val Lys Ala
                245                 250                 255

Leu Ser Arg Ala Met Leu Leu Thr Ser Tyr Leu Pro Pro Pro Leu Leu
            260                 265                 270

Arg His Arg Leu Lys Thr His Thr Val Ile His Gln Leu Asp Lys
            275                 280                 285

Ala Leu Ala Lys Leu Gly Ile Gly Gln Leu Thr Ala Gln Glu Val Lys
290                 295                 300

Ser Ala Cys Tyr Leu Arg Gly Leu Asn Ser Thr His Ile Gly Glu Asp
305                 310                 315                 320

Arg Cys Arg Thr Trp Leu Gly Glu Trp Leu Gln Ile Ser Cys Ser Leu
                325                 330                 335

Lys Glu Ala Glu Leu Ser Leu Leu His Asn Val Val Leu Leu Ser
            340                 345                 350

Thr Asn Tyr Leu Gly Thr Arg Arg
            355                 360

<210> SEQ ID NO 3
<211> LENGTH: 18
<212> TYPE: DNA
<213> ORGANISM: Artificial Sequence
<220> FEATURE:
<223> OTHER INFORMATION: oligonucleotide which specifically binds to
                        HCCR-1 mRNA

<400> SEQUENCE: 3
cctggacatt ttgtcacc                                              18

<210> SEQ ID NO 4
<211> LENGTH: 25
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (10)..(15)
<223> OTHER INFORMATION: restriction site of BamHI

<400> SEQUENCE: 4
aggcaactag gatccaggca tttct                                      25

<210> SEQ ID NO 5
<211> LENGTH: 29
<212> TYPE: DNA
<213> ORGANISM: Artificial Sequence
<220> FEATURE:
<223> OTHER INFORMATION: PCR primer
```

```
<220> FEATURE:
<221> NAME/KEY: misc_feature
<222> LOCATION: (1)..(6)
<223> OTHER INFORMATION: restriction site of SalI

<400> SEQUENCE: 5
gtcgacgcag ttcccacagg tgtgccatg                                              29
```

US 7,459,602 B2

MAMMALIAN CANCER CELL AND TRANSGENIC MAMMAL CARRYING HUMAN PROTOONCOGENE AND KIT FOR DIAGNOSING CANCER USING SAID PROTOONCOGENE

FIELD OF THE INVENTION

The present invention relates to a mammalian cancer cell transformed with an expression vector comprising a human protooncogene having the nucleotide sequence of SEQ ID NO: 1; a mammalian embryo comprising a nucleic acid construct containing the protooncogene; a transgenic cancered mammal derived from the mammalian embryo; and a kit for diagnosing breast, kidney, ovary or stomach cancer using the protooncogene.

BACKGROUND OF THE INVENTION

Higher animals including man each carry approximately 100,000 genes, but only about 15% thereof is expressed, and characteristics of individual's biological process, e.g., genesis, differentiation, homeostasis, responses to stimuli, control of cell cycle, aging and apoptosis (programmed cell death), are determined depending on which genes are expressed (Liang, P. and A. B. Pardee, *Science,* 257: 967-971 (1992)).

Pathogenic phenomena such as tumorigenesis are caused by gene mutation which brings about changes in the mode of gene expression.

It has been reported that tumorigenesis is caused by various genetic changes such as the loss of chromosomal heterozygosity, activation of oncogenes and inactivation of tumor suppressor genes, e.g., p53 gene (Bishop, J. M., *Cell,* 64, 235-248 (1991); and Hunter, T., *Cell,* 64, 249-270 (1991)). Further, it has been reported that 10 to 30% of human cancer arises from the activation of oncogene through amplification of protooncogenes.

Therefore, the activation of protooncogenes plays an important role in the etiology of many tumors and there has existed a need to identify protooncogenes.

The present inventor reported that a protooncogene, human cervical cancer 1 (HCCR-1), is specifically overexpressed in cancer cells (Korean Patent Laid-open Publication No. 2001-39566). In order to unravel the mechanism involved in the tumorigenesis, the present inventor has endeavored to prepare a cancer cell line and a transgenic mammal developing cancer using HCCR-1 protooncogene.

SUMMARY OF THE INVENTION

Accordingly, it is an object of the present invention to provide a mammalian cell having introduced HCCR-1 protooncogene.

Another object of the present invention is to provide a mammalian embryo carrying HCCR-1 protooncogene, and a transgenic mammal derived from the mammalian embryo.

A further object of the present invention is to provide a kit for diagnosing breast, kidney, ovary or stomach cancer using HCCR-1 protooncogene.

In accordance with one aspect of the present invention, there is provided a mammalian cell transformed with an expression vector comprising human protooncogene HCCR-1 which has the nucleotide sequence of SEQ ID NO: 1.

BRIEF DESCRIPTION OF THE DRAWINGS

The above objects and features of the present invention will become apparent from the following description of preferred embodiments taken in conjunction with the accompanying drawings, in which.

DETAILED DESCRIPTION OF THE INVENTION

Figure 1A:
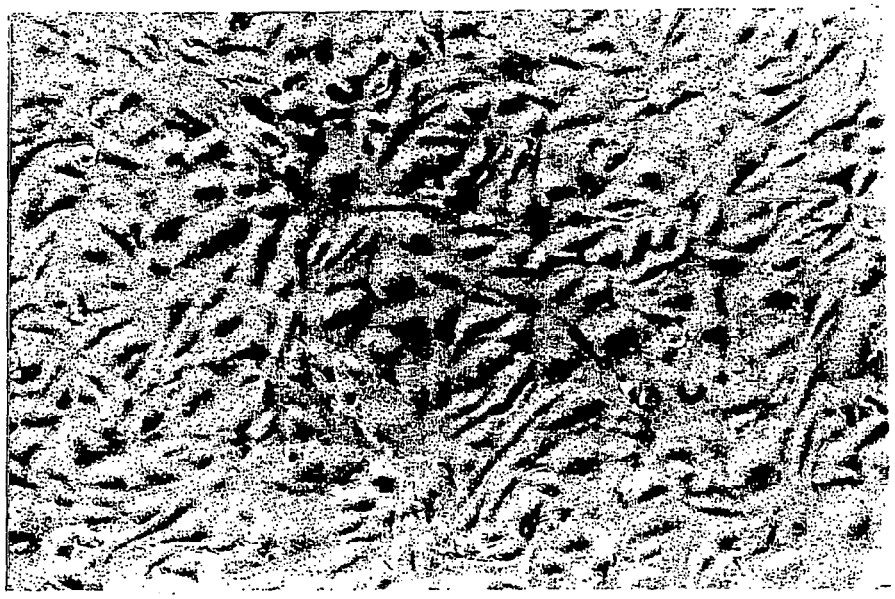
FIGS. 1A and 1B are the respective phase-contrast features of monolayer-cultured HCCR-1M and parental wild-type NIH/3T3 cells.

The human protooncogene (hereinafter "HCCR-1 protooncogene") of SEQ ID NO: 1 which is used in the preparation of the inventive mammalian cell and transgenic mammal is located on the long arm (12q) of the 12th chromosome and has an open reading frame which encodes a protein having the amino acid sequence of SEQ ID NO: 2 and molecular weight of about 50 kDa.

In consideration of the degeneracies of codons and the preferred codons in a specific animal wherein the HCCR-1 protooncogene is to be expressed, various changes and modifications of the nucleotide sequence of SEQ ID NO:1 may be made, e.g., in the coding region thereof without adversely altering the amino acid sequence of the expressed protein, or in the non-coding region without adversely affecting the expression of the HCCR-1 protooncogene. Therefore, the present invention also includes, in its scope, a polynucleotide having substantially the same base sequence as the HCCR-1 protooncogene, and a fragment thereof. As used herein, "substantially the same polynucleotide" refers to a polynucleotide whose base sequence shows 80% or more, preferably 90% or more, most preferably 95% or more homology to the HCCR-1 protooncogene.

The HCCR-1 protooncogene can be obtained from human cancer tissues or synthesized using a conventional DNA synthesis method. Further, the HCCR-1 protooncogene thus prepared may be inserted to a conventional vector to obtain an expression vector.

The expression vector may, in turn, be introduced into a suitable mammalian cell to obtain a mammalian cell transfected with the expression vector. For example, NIH/3T3 cells (ATCC CRL 1658), a differentiated mouse fibroblast cell line, and 293 cells (ATCC CRL 1573), a human embryonic kidney cell line, were transfected with expression vector pcDNA3/HCCR-1 containing the HCCR-1 protooncogene to obtain the NIH/3T3 and 293 cells transfected with HCCR-1 protooncogene, designated HCCR-1M and HCCR-1H cells, respectively, which were deposited with Korean Collection for Type Cultures (KCTC) (Address: #52, Oun-dong, Yusong-ku, Taejon 305-333, Republic of Korea) on Dec. 26, 2000 under the accession numbers of KCTC 0923BP and KCTC 0922BP, respectively, in accordance with the terms of Budapest Treaty on the International Recognition of the Deposit of Microorganism for the Purpose of Patent Procedure.

The inventive mammalian cell thus obtained overexpresses HCCR-1 protooncogene and exhibits morphological characteristics of tumor giant cells. Specially, mouse cell HCCR-1M has a polygonal shape, lobulated nucleus with prominent nucleoli, well developed rough endoplasmic reticula (rER) and Golgi complexes, and microvilli on the cell surface, and exhibits atypical mitotic figures. The human cell HCCR-1H has increased cell dimension and cellularity compared with the wild-type cell.

The inventive mammalian cell has a tumorigenicity and therefore a mammal grafted with the inventive mammalian cell develops a tumor, e.g., palpable tumor. Further, a mammalian cell isolated from the tumor has a tumorigenicity. For example, a mouse cell, designated HCCR-1MN, isolated from a palpable tumor of a nude mouse grafted with HCCR-1M cell has the morphological features similar with those of HCCR-1M cell.

The inventive mammalian cell produces a large amount of HCCR-1 protein which interacts with D52 protein (GenBank accession number NM003288) which has been reported to be associated with breast carcinoma (Byrne, J. A., et al., *Cancer Res.*, 55, 2896-2903 (1995); and Byrne, J. A., et al., *Oncogene*, 16, 873-881 (1998)). It also enhances a cellular protein kinase C (PKC) and telomerase activities, induces the loss of particular cell cycle checkpoint controls, and suppresses the egr-1 expression, thereby predisposing cells to malignant conversion. In this process, the expression of p53 tumor suppressor gene involved in the cell cycle control increases while most of the p53 proteins are inactivated, thereby leading to malignant conversion. The HCCR-1 protooncogene induces functional inactivation of p53 tumor suppressor at an upstream level. Therefore, if a portion of HCCR-1 protooncogene which regulates p53 gene is identified, the p53 activity may be recovered by changing the corresponding nucleotide sequence.

Further, a nucleic acid construct comprising HCCR-1 protooncogene may be introduced into a suitable embryo of a mammal, e.g., a mouse, and the mammalian embryo thus obtained may be implanted in the uterus of a suitable recipient and allowed to develop to term to obtain a transgenic mammal. The method for preparing a transgenic mammal is well known in the art, and it is preferable to introduce the nucleic acid construct into an embryo at the 8-cell stage or earlier.

The transgenic mammal thus prepared overexpresses HCCR-1 protooncogene and develops ductal papillary adenocarcinoma of breast exhibiting the charachteristic features of: well-circumscribed nodule without capsule; papillary structures and glandular or duck-like structures; extensive necrosis occurring in the central portion; cuboid or ovoid cells having indistinct borders; normal breast tissues being adjacent thereto; and a significant amount of granular, eosinophilic cytoplasm.

A transgenic embryo may be obtained by mating male and female transgenic mammals. An exemplary transgenic embryo is mouse FVB/N embryo (designated mouse embryo HCCR-1) carrying the nucleic acid construct having the structure of FIG. 21, which was deposited with the Korean Collection for Type Cultures (KCTC) (Address: #52, Oun-dong, Yusong-ku, Taejon 305-333, Republic of Korea) on Dec. 26, 2000 under the accession number of KCTC 0924BP, in accordance with the terms of Budapest Treaty on the International Recognition of the Deposit of Microorganism for the Purpose of Patent Procedure.

Since the inventive mammalian cell and transgenic mammal overexpresses HCCR-1 protooncogene to develop cancer, they are advantageously used in screening a carcinogen or anti-cancer agent, e.g., antioxidant.

Further, HCCR-1 protooncogene is overexpressed in breast, kidney, ovary and stomach cancers, and therefore, the product thereof may be effectively used in diagnosing the cancers. The cancer diagnosis may be conducted by reacting mRNA or a protein sample taken from breast, kidney, ovary or stomach tissue of a subject with a probe or antibody which specifically binds to mRNA or the protein expressed from the HCCR-1 protooncogene; and detecting the HCCR-1 mRNA or protein according to various methods known in the art, thereby determining whether the subject has overexpressed products of HCCR-1 protooncogene. The presence of the protooncogene product may be easily detected by labeling the probe or antibody with a radioisotope or an enzyme. Therefore, the present invention also provides a kit for diagnosing a breast, kidney, ovary or stomach cancer, which comprises a probe or an antibody which specifically binds to an mRNA or protein expressed from HCCR-1 protooncogene. Exemplary probes include a polynucleotide or oligonucleotide which has a nucleotide sequence complementary to mRNA transcribed from the HCCR-1 protooncogene or a portion of the mRNA so that it specifically binds to the HCCR-1 mRNA, and preferred is that having the nucleotide sequence of SEQ ID NO: 3. The probe can be obtained from human tissues or synthesized using a conventional DNA synthesis method. Further, the antibody can be prepared according to conventional method kwon in the art.

The following Examples are intended to further illustrate the present invention without limiting its scope.

REFERENCE EXAMPLE 1

Transmission Electron Microscopy (TEM)

Cells or tissues were fixed with 2.5% glutaraldehyde in a phosphate buffer (pH 7.4) and then postfixed with a 2% osmium tetroxide. Specimens were dehydrated in a graded series of ethanols and embedded in Epon 812. Ultrathin sections thereof were stained with uranyl acetate and lead citrate, and photographed by TEM (JEOL 1,200 EX, Tokyo, Japan).

REFERENCE EXAMPLE 2

Western Blot Analysis

Cells were harvested and lysed in a Laemmli sample buffer in accordance with the method described by Laemmli (*Nature*, 227, 680-685 (1970)). The cellular proteins were separated by 10% SDS-PAGE and then electroblotted onto nitrocellulose membranes. The membranes were incubated with the antibody. After washing, the membranes were incubated with a blocking solution containing 1:1,000 dilution of peroxidase-conjugated goat anti-rat immunoglobulin (Jackson ImmunoResearch) as a secondary antibody. Proteins were revealed by an ECL-Western blot detection kit (Amersham).

REFERENCE EXAMPLE 3

Immunohistochemical Analysis

Tissues were incubated with a primary antibody and then cut in a thickness of 5 μm. Binding of primary antibody was visualized by biotinylated secondary antibody, avidin, biotinylated horseradish peroxidase and AEC (aminoethyl carbazole) as the chromogen (HISTOSTAIN-BULK KITS, Zymed).

REFERENCE EXAMPLE 4

Isolation of Total RNA

Total RNAs were extracted from the tissue specimens or cells using a commercial system (RNeasy total RNA kit, Qiagen Inc., Germany), and DNA contaminants were removed therefrom using Message clean kit (GenHunter Corp., USA).

REFERENCE EXAMPLE 5

Northern Blot Analysis

20 μg of the total RNAs were electrophoresed through 1% formaldehyde agarose gel and transferred to nylon membranes (Boehringer-Mannheim, Germany). The blot was hybridized overnight at 42° C. with $^{32}$P-labeled random-primed probe which was prepared using a rediprime II random prime labeling system (Amersham, UK). The northern blot analysis results were consistently repeated two times, as quantified by densitometry and the same blot was hybridized with a β-actin probe to confirm mRNA integrity.

PREPARATION EXAMPLE 1

Construction of Expression Vector Containing HCCR-1 Protooncogene

*E. coli* JM-109/HCCR1 (KCTC 0667BP) has expression vector pCEV-LAC/HCCR-1 containing the full length HCCR-1 cDNA represented by the nucleotide sequence of SEQ ID NO: 1. *E. coli* JM-109/HCCR1 cells were cultured and expression vector pCEV-LAC/HCCR-1 was isolated therefrom. Expression vector pCEV-LAC/HCCR-1 thus obtained was cleaved with SalI to obtain a 2.1 kb DNA fragment containing the full length HCCR-1 cDNA.

Mammal expression vector pcDNA3 (Invitrogene) was cleaved with XhoI to make a compatible end with SalI. The 2.1 kb SalI fragment was ligated with the XhoI-digested pcDNA3 to obtain expression vector pcDNA3/HCCR-1 containing the full length HCCR-1 cDNA.

PREPARATION EXAMPLE 2

Production of Anti-HCCR-1 Antibody

In order to obtain HCCR-1 proteins useful in the preparation of anti-HCCR-1 antibody, *E. coli* JM-109/HCCR1 (KCTC 0667BP) cells were cultured and expression vector pCEV-LAC/HCCR-1 was isolated therefrom. Expression vector pCEV-LAC/HCCR-1 was subjected to polymerase chain reaction (PCR) using primers of SEQ ID Nos: 4 and 5 to amplify a DNA region from the 123rd to the 473rd nucleotides of SEQ ID NO: 1 (the 39th to the 155th amino acid residues of SEQ ID NO: 2). The PCR product thus obtained was inserted at BamHI/SalI sites of vector pMAL-p2 (New England Biolab, USA) to obtain a recombinant vector (designated pMAL-p2/HCR-1-c-terminal), and then, *E. coli* BL21 (ATCC CRL 47092) was transformed with recombinant vector pMAL-p2/HCCR-1-c-terminal. The transformant was cultured in LB media and the resulting culture was diluted with 100-fold volume of LB media. The diluted culture was incubated for 3 hours, and then, 1 mM isopropyl β-D-thiogalacto-pyranoside (IPTG, Sigma) was added thereto to induce expression of HCCR-1 protooncogene. The C-terminal portion of HCCR-1 protein fused with maltose binding protein (MBP, 42 kDa) derived from vector pMAL-p2 was expressed which has the molecular weight of approximate 64 kDa. The 64 kDa fusion protein was purified from the culture using pMAL protein fusion and purification system (New England Biolab., USA).

Then, ten 3-month-old New Zealand white rabbits each weighing about 2.5 kg were intraperitoneally administered with 1 mg of the fusion protein weekly for 3 times. The blood sample was obtained from the immunized rabbits and centrifuged to obtain a serum containing a polyclonal antibodies.

EXAMPLE 1

Preparation of Mouse Cell Transfected with HCCR-1 Protooncogene

NIH/3T3 cells (ATCC CRL 1658), differentiated mouse fibroblast cell line, were transfected with expression vector pcDNA3/HCCR-1 obtained in Preparation Example 1 using Lipofectamine (Gibco BRL), and the resulting NIH/3T3 cells were cultured in Waymouth MB 752/1 medium supplemented with G418 (Gibco) to obtain the NIH/3T3 cell transfected with HCCR-1 protooncogene, designated HCCR-1M, which was deposited with Korean Collection for Type Cultures on Dec. 26, 2000 under the accession number of KCTC 0923BP.

EXAMPLE 2

Preparation of Human Cell Transfected with HCCR-1 Protooncogene

The procedure of Example 1 was repeated except that 293 cells (ATCC CRL-1573) were used instead of NIH/3T3 cells, to obtain the 293 cell transfected with HCCR-1 protooncogene, designated HCCR-1H, which was deposited with Korean Collection for Type Cultures on Dec. 26, 2000 under the accession number of KCTC 0922BP.

COMPARATIVE EXAMPLE

Preparation of Comparative Cell Transfected with Vector pcDNA3

The procedure of Example 1 was repeated except that vector pcDNA3 (Invitrogen) was used instead of vector pcDNA3/HCCR-1 to obtain comparative cells transfected with vector pcDNA3.

EXAMPLE 3

Morphological Characteristics of HCCR-1 M Cell (Step 1) Phase-contrast features of HCCR-1M cell HCCR-1M cells obtained in Example 1 were cultured in monolayer in Waymouth MB 752/1 medium and the resulting HCCR-1M cells were examined under the phase-contrast microscope. The parental wild-type NIH/3T3 cells were used as a control.

Figure 1B:
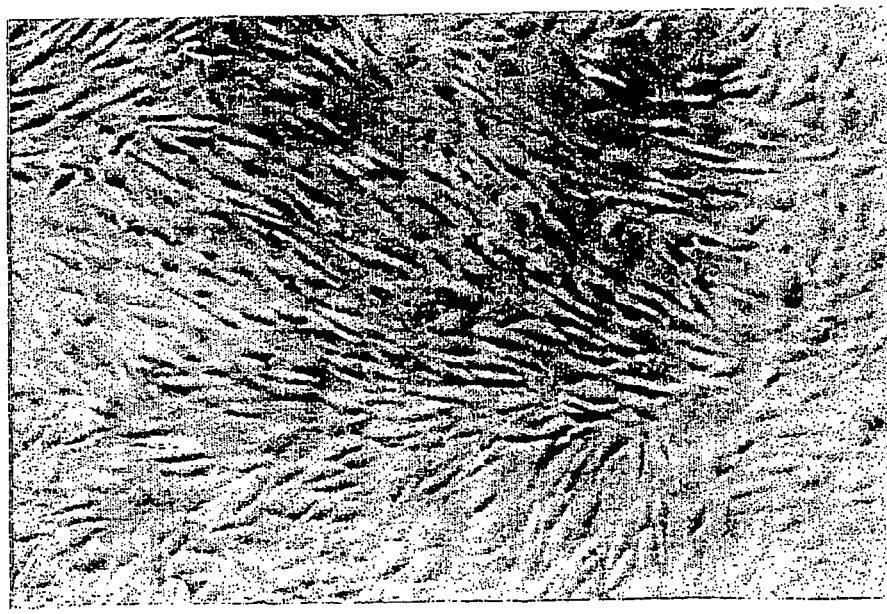

FIGS. 1A and 1B are the respective phase-contrast features of monolayer-cultured HCCR-1M and parental wild-type NIH/3T3 cells. As can be seen from FIGS. 1A and 1B, the parental wild-type NIH/3T3 cells are spindle shaped cells having a long slender nucleus and a scanty amount of cytoplasm, while HCCR-1M cells have a polygonal shape with an ovoid nucleus and plump cytoplasm.

(Step 2) Hematoxylin-eosin Staining

HCCR-1M cells obtained in Example 1 were cultured in monolayer in Waymouth MB 752/1 medium and the resulting HCCR-1M cells were stained with hematoxylin-eosin.

Figure 2:
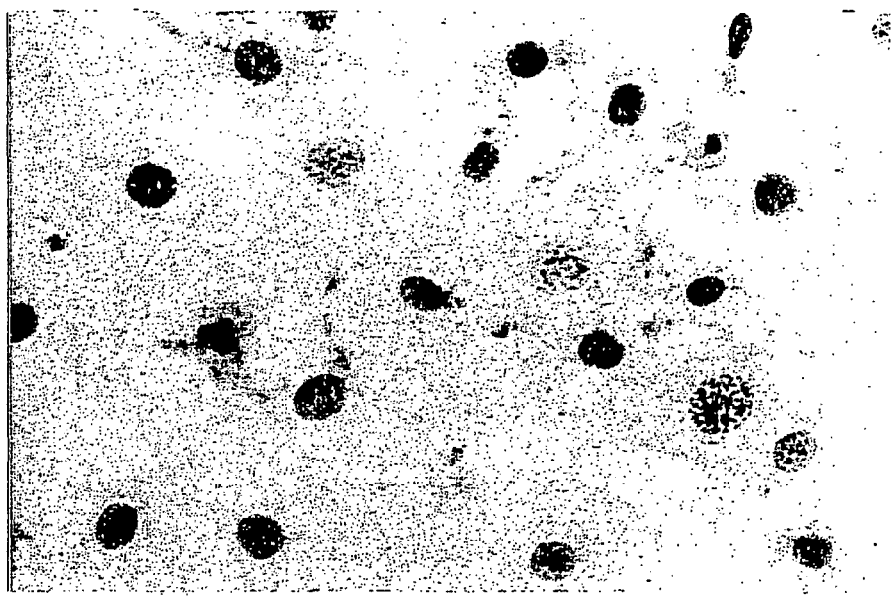
FIG. 2 is the hematoxylin-eosin staining result of monolayer-cultured HCCR-1M cells.

FIG. 2 is the hematoxylin-eosin staining result of monolayer-cultured HCCR-1M cells. As can be seen from FIG. 2, HCCR-1M cells exhibit nuclear pleiomorphism, distinct nucleoli, granular chromatin patterns, tumor giant cells and atypical mitotic figures.

(Step 3) TEM

HCCR-1M cells obtained in Example 1 were subjected to TEM according to the procedure of Reference Example 1.

Figure 3:
FIG. 3 is a transmission electron microscope picture of HCCR-1M cells.

FIG. 3 is the TEM picture of HCCR-1M cell wherein the scale bar represents the length of 3 μm and the inset is higher magnification of area indicated by circle (scale bar, 1 μm). As can be seen from FIG. 3, the HCCR-1M cells have microvilli on the cell surface, lobulated nucleus with prominent nucleoli and well-developed rough endoplasmic reticula (rER) and Golgi complexes (circle).

The above results show that HCCR-1M cell has morphological characteristics of tumor giant cell.

EXAMPLE 4

Tumorigenicity of HCCR-1M cell $5 \times 10^6$ each of HCCR-1M cells obtained in Example 1 were injected subcutaneously into the posterior lateral aspect of the trunk of 9 nude mice (5-week-old athymic nu/nu on BALB/c background).

Figure 4:
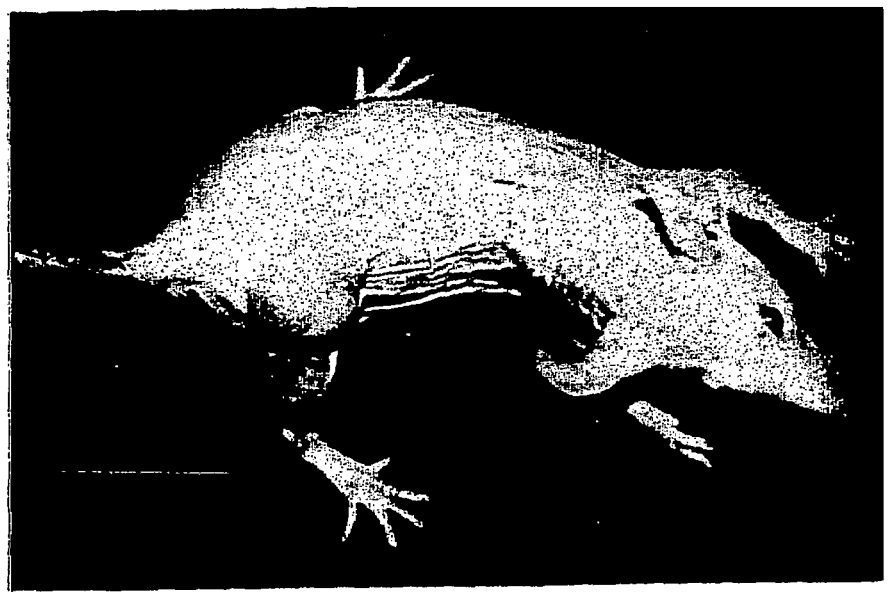
FIG. 4 is a photograph of the nude mouse allografted with HCCR-1M cells showing the palpable tumor nodule.

All 9 nude mice injected with HCCR-1M cells showed palpable tumors after 21 days. FIG. 4 is the photograph of the nude mouse allografted with HCCR-1M cells. This suggests that the HCCR-1M cells have a tumorigenicity.

When the subcutaneous tumors reached 1.5-2.5 cm in diameter, the nude mice were sacrificed and the tumors were removed therefrom which was used in the following tumor analysis and establishment of cell line.

EXAMPLE 5

Characteristics of Tumor Nodule of Nude Mouse Grafted with HCCR-1M Cell

Characteristics of nude mouse's tumor nodules induced by HCCR-1M allograft were examined as follows.

(Step 1) Hematoxylin-eosin Staining

The tumor nodules obtained in Example 4 were stained with hematoxylin-eosin staining.

Figure 5:
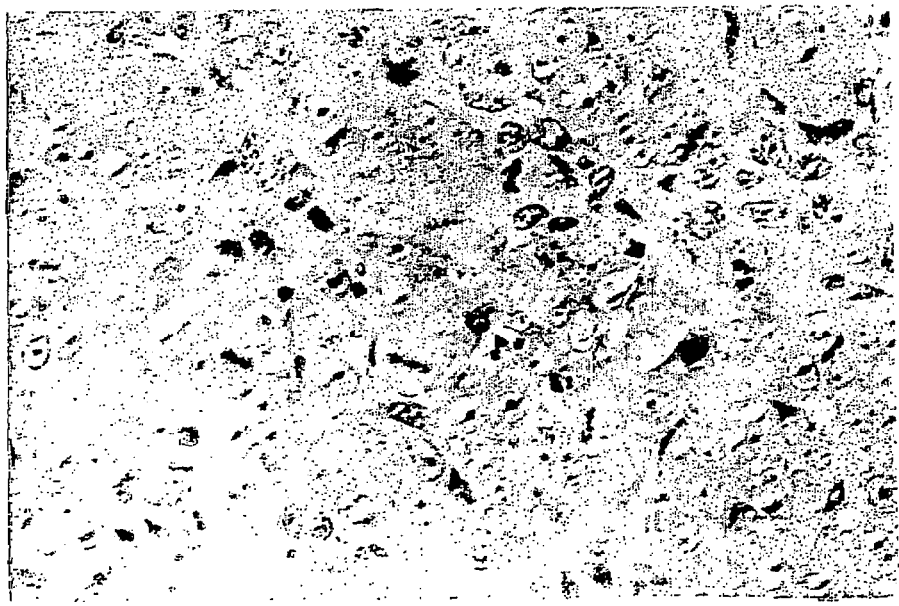
FIG. 5 is the hematoxylin-eosin staining result of the palpable tumor nodules taken from the nude mouse allografted with HCCR-1M cells.

FIG. 5 is the hematoxylin-eosin staining result (×250) of the tumor nodules. As can be seen from FIG. 5, the tumor nodules have typical epithelial cell nests separated by fibrous stroma.

(Step 2) TEM

The tumor nodules obtained in Example 4 were subjected to TEM according to the procedure of Reference Example 2.

Figure 6:
FIG. 6 is a transmission electron microscope picture of the palpable tumor nodules taken from the nude mouse allografted with HCCR-1M cells.

FIG. 6 is the TEM picture of the tumor nodules wherein the scale bar has the length of 3 μm and the inset is higher magnification of area indicated by circle (scale bar, 0.5 μm). As can be seen from FIG. 6, the cells of tumor nodules have well-developed organelles and are tightly connected by desmosomes. This suggests that the HCCR-1M cells were changed into epidermal cells.

(Step 3) Immunohistochemical Analysis

The tumor nodules obtained in Example 4 were subjected to immunohistochemistry according to the procedure of Reference Example 3 using each of anti-reticulin fiber, anti-keratin, anti-EMA (epithelial membrane antigen) and anti-vimentin antibodies (DAKO) as a primary antibody.

Figure 7A:
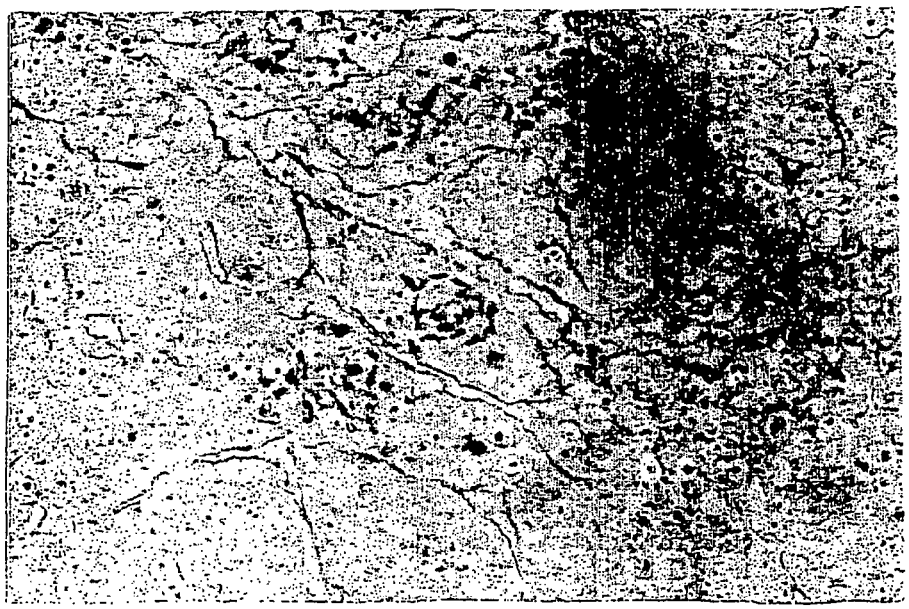
FIGS. 7A to 7D are the immunohistochemical analysis results showing the expression of reticulin fibers, keratin, epithelial membrane antigen and vimentin, respectively, in the palpable tumor nodules taken from the nude mouse allografted with HCCR-1M cells.
Figure 7B:
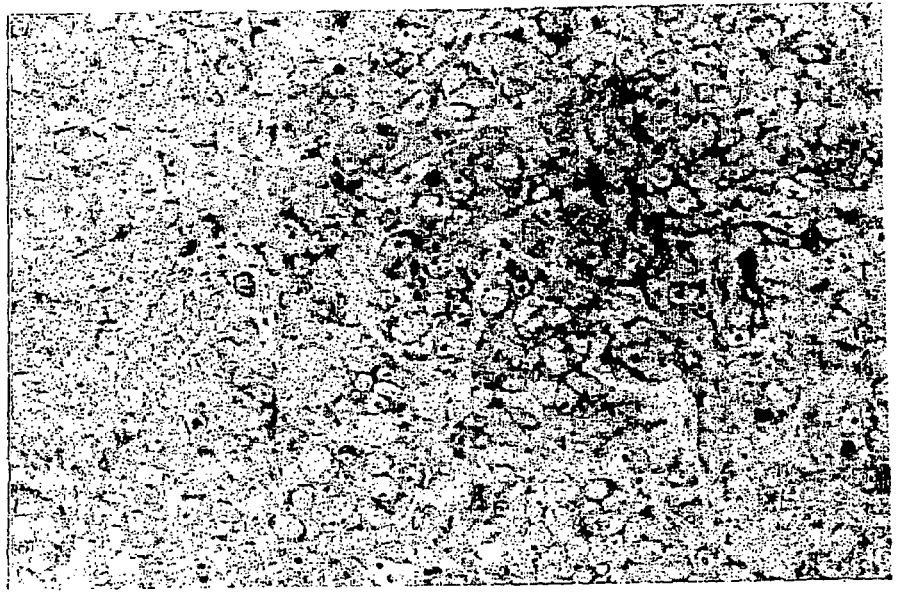
Figure 7C:
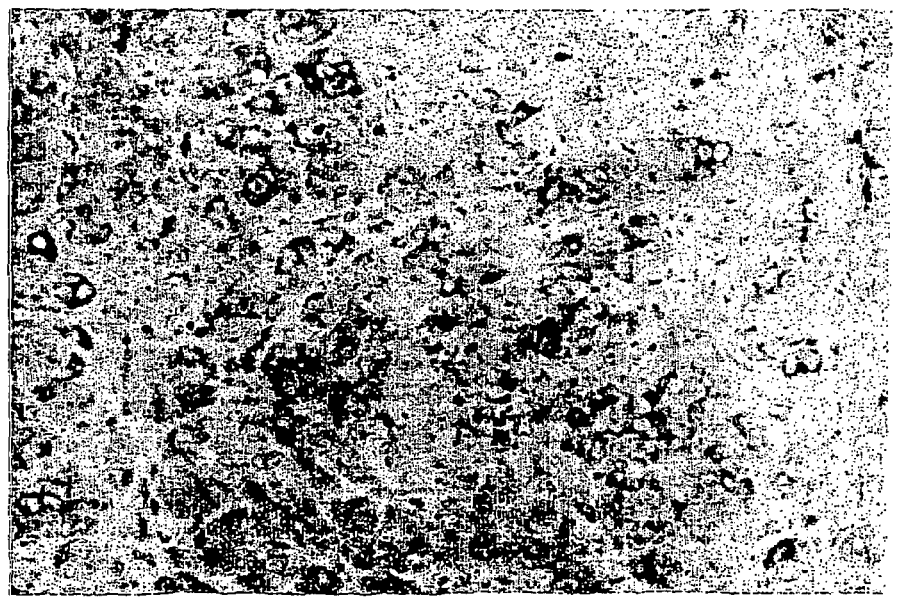
Figure 7D:
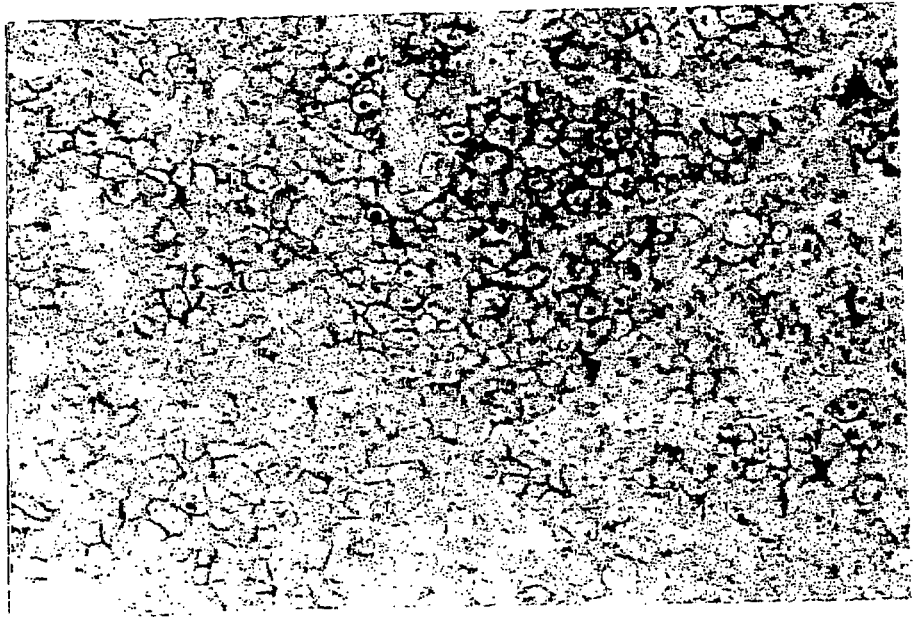

FIGS. 7A to 7D are the immunohistochemical analysis results (×250) showing the expression of reticulin fibers, keratin, EMA and vimentin, respectively, in the tumor nodules. As can be seen from FIGS. 7A to 7D, the cell nests were enveloped by reticulin fibers (FIG. 7A) and the cells showed coexpression of epithelial markers, such as keratin (FIG. 7B) and EMA (FIG. 7C) and of the mesenchymal marker, vimentin (FIG. 7D). These results suggest that HCCR-1 protooncogene caused the conversion of the mesenchymal NIH/3T3 cells to epithelial cells.

Particularly, the mesenchymal NIH/3T3 cell introduced with an oncogene transforms into sarcoma, whereas the nude mouse allografted with HCCR-1M cell develops a palpable tumor.

EXAMPLE 6

Preparation of Cancer Cell Line from Nude Mouse Allografted with HCCR-1M cell

Cells were isolated from the tumor nodules obtained in Example 4 and then cultured in Waymouth MB 752/1 medium supplemented with 20% bovine fetal serum, which were designated HCCR-1MN cell.

EXAMPLE 7

Characteristics of HCCR-1MN Cells

The HCCR-1MN cells obtained in Example 6 were subjected to phase-contrast microscopy by repeating the procedure of Step 1 of Example 3.

Figure 8:
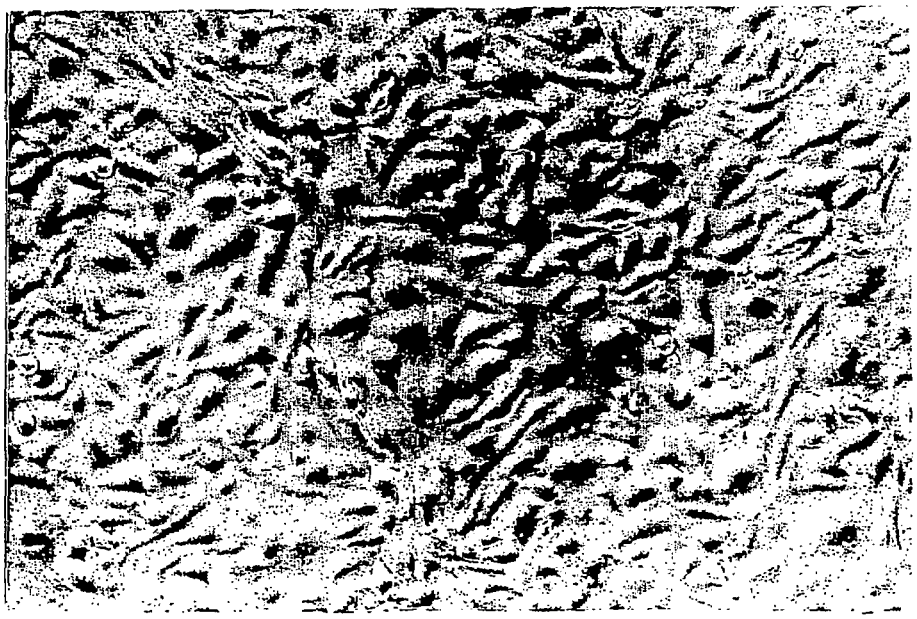
FIG. 8 is a phase-contrast feature of monolayer-cultured HCCR-1MN cells.

FIG. 8 is the phase-contrast feature (×300) of monolayer-cultured HCCR-1MN cells. As can be seen from FIG. 8, HCCR-1MN cells have morphological characteristics similar with those of HCCR-1M cells represented in Step 1 of Example 3.

EXAMPLE 8

Western Blot Analyses of HCCR-1M and HCCR-1MN Cells

To examine expression of HCCR-1 protooncogene in HCCR-1M and HCCR-1MN cells, HCCR-1M and HCCR-1MN cells obtained in Examples 1 and 6, respectively, were subjected to western blot analysis according to the procedure of Reference Example 2 using the anti-HCCR-1 serum obtained in Preparation Example 2. For the comparison, the parental wild-type NIH/3T3 cells and the comparative NIH/3T3 cells obtained in Comparative Example were used in the western blot analysis.

Figure 9:
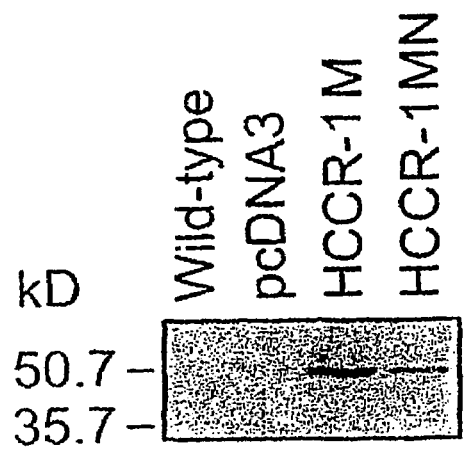
FIG. 9 is the western blot analysis result showing the expression of HCCR-1 protooncogene in HCCR-1M and HCCR-1MN cells.

FIG. 9 is the western blot analysis result showing the expression of HCCR-1 protooncogene in HCCR-1M and HCCR-1MN cells. As can be seen from FIG. 9, the HCCR-1 protein is overexpressed in HCCR-1M and HCCR-1MN cells, but not in the parental wild-type NIH/3T3 cells and comparative NIH/3T3 cells transfected with vector pcDNA3, as represented as weak band.

EXAMPLE 9

Characteristics of HCCR-1H Cell

To examine morphological characteristics of HCCR-1H cell, the HCCR-1H cells were subjected to phase-contrast microscopy according to the procedure of Step 1 of Example 3. The parental wild-type 293 cells were used as a control.

Figure 10A:
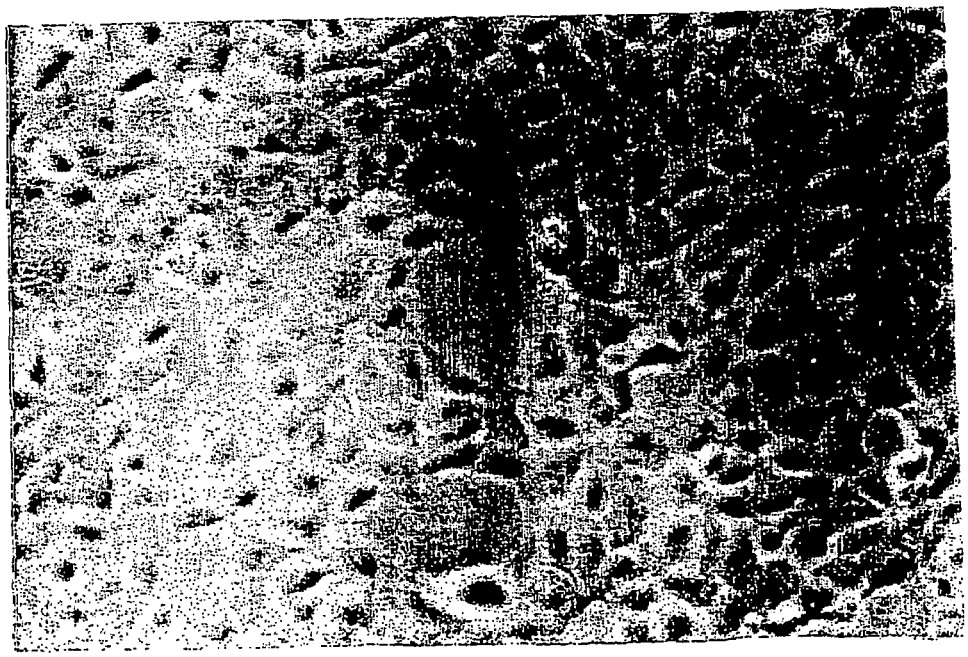
FIGS. 10A and 10B are the phase-contrast features of monolayer-cultured HCCR-1H and parental wild-type 293 cells, respectively.
Figure 10B:
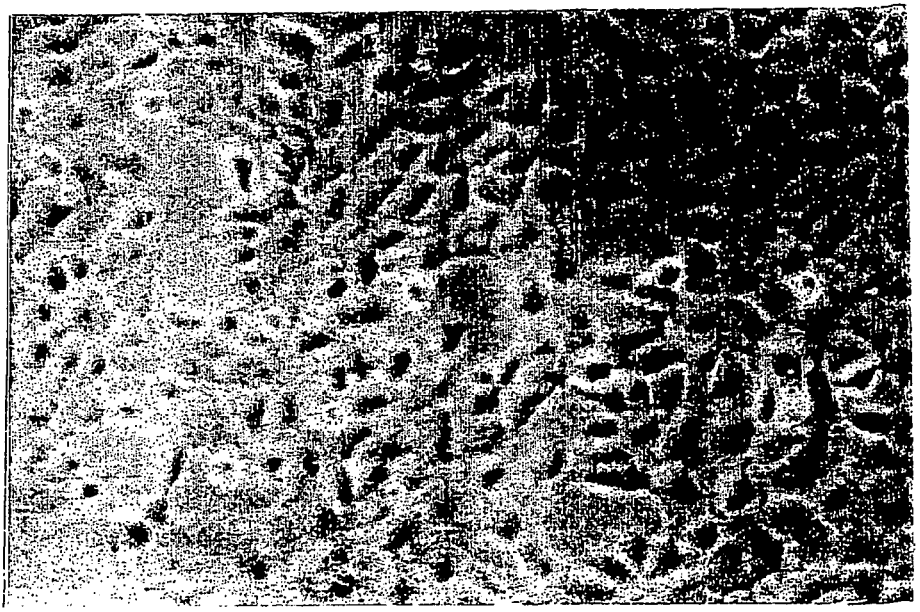

FIGS. 10A and 10B are the respective phase-contrast features (×300) of monolayer-cultured HCCR-1H and parental wild-type 293 cells. As can be seen from FIGS. 10A and 10B, the HCCR-1H cell has increased cell dimension and cellularity compared with the wild-type 293 cell.

EXAMPLE 10

Tumorigenicity of HCCR-1H Cell

To examine tumorigenicity of HCCR-1H cell, the procedure of Example 4 was repeated using HCCR-1H cells obtained in Example 2.

Nude mice xenografted with HCCR-1H cells showed palpable tumors after 21 days. This suggests that the HCCR-1H cell has a tumorigenicity.

When the tumors reached 1-1.5 cm in diameter, the nude mice were sacrificed and the tumors were removed therefrom which was used in the following tumor analysis.

EXAMPLE 11

Characteristics of Tumor Nodule of Nude Mouse Grafted with HCCR-1H Cell

Characteristics of nude mouse's tumor nodules induced by HCCR-1H allograft were examined as follows.

(Step 1) Hematoxylin-eosin Staining

The tumor nodules obtained in Example 10 were stained with hematoxylin-eosin staining.

Figure 11:
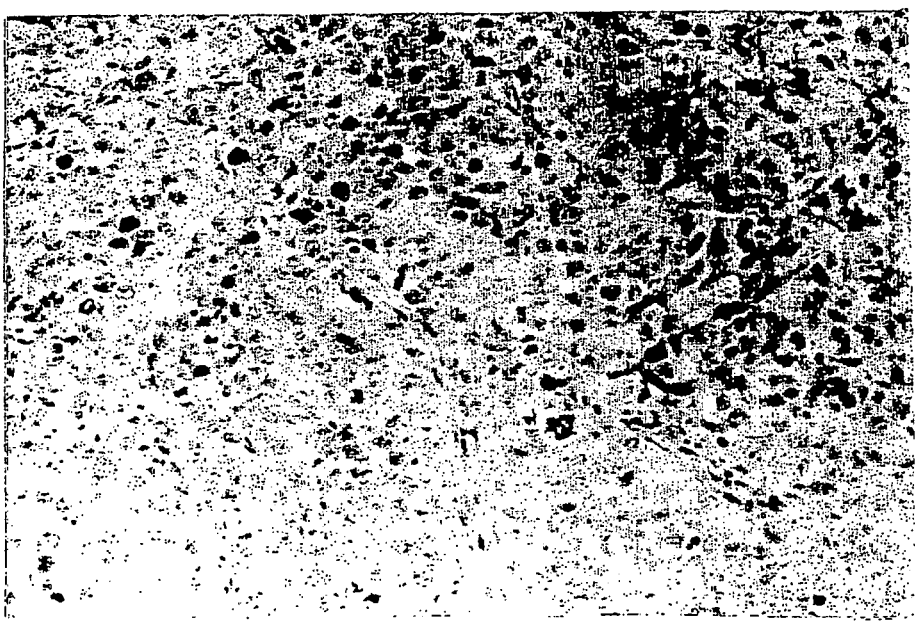
FIG. 11 is the hematoxylin-eosin staining result of the palpable tumor nodules taken from the nude mouse xenografted with HCCR-1H cells.

FIG. 11 is the hematoxylin-eosin staining result (×250) of the palpable tumor nodules. As can be seen from FIG. 11, the tumor nodule has characteristics of typical epithelial cell carcinomas, i.e., atypism of cell shape, pleomorphism, nucleolar enlargement, and increased volume ratio of nucleus to cytoplasm.

(Step 2) immunohistochemical Analysis

The tumor nodules obtained in Example 10 were subjected to immunohistochemistry according to the procedure of Reference Example 3 using each of anti-cytokeratin-8, anti-cytokeratin-19 and anti-vimentin antibodies (DAKO) as a primary antibody.

Figure 12A:
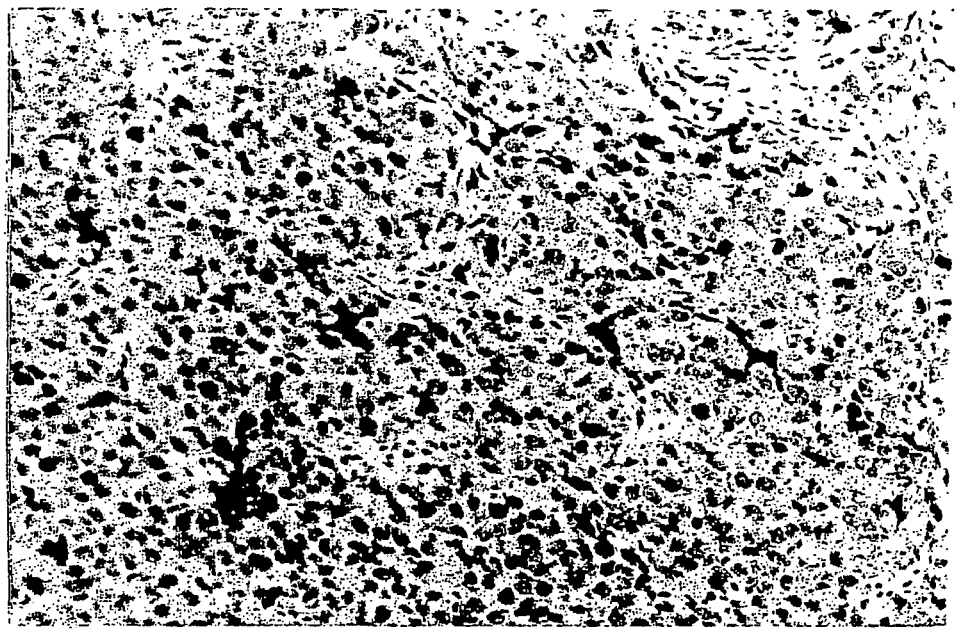
FIGS. 12A to 12C are the immunohistochemical analysis results showing the expression of cytokeratin 8, cytokeratin 19 and vimentin, respectively, in the palpable tumor nodules taken from the nude mouse xenografted with HCCR-1H cells.
Figure 12B:
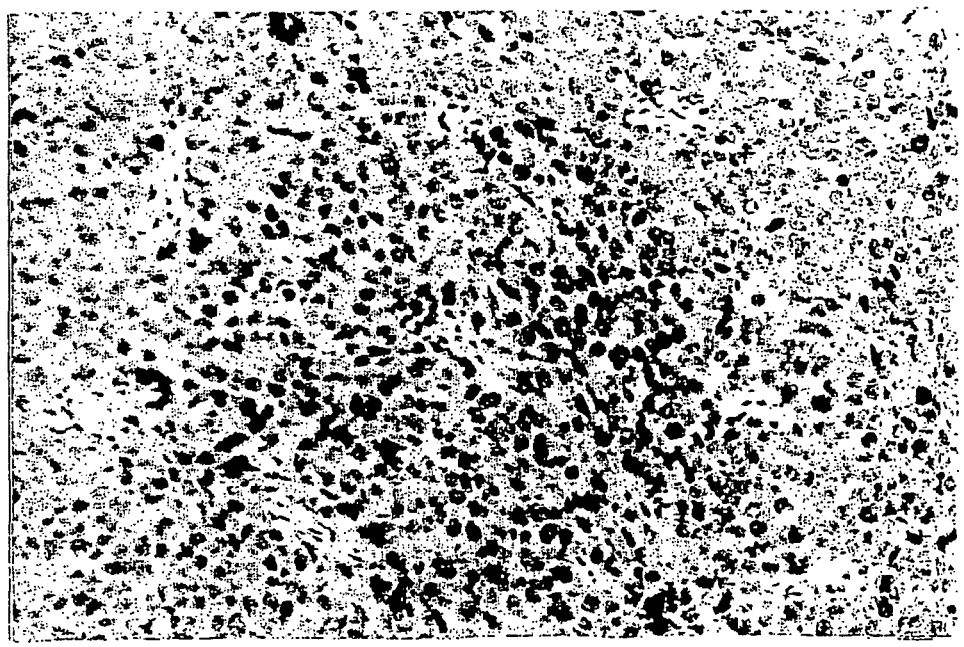
Figure 12C:
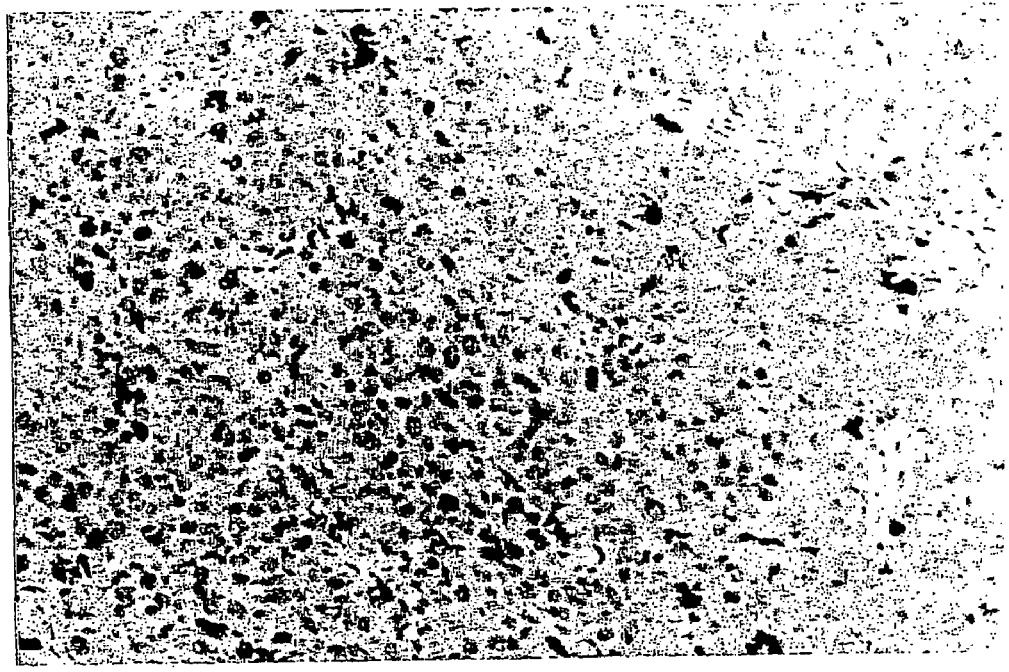

FIGS. 12A to 12C are the immunohistochemical analysis results (×250) showing the expression of cytokeratin 8, cytokeratin 19 and vimentin, respectively, in the palpable tumor nodules. As can be seen from FIGS. 12A to 12C, the tumor cells showed coexpression of epithelial markers, such as cytokeratin-8 and -19 (FIGS. 12A and 12B), and the mesenchymal marker, vimentin (FIG. 12C). These results suggest that HCCR-1 protooncogene caused the conversion of the mesenchymal 293 cells to epithelial cells.

EXAMPLE 12

Northern Blot Analysis of HCCR-1H Cell

To examine expression level of HCCR-1 protooncogene in HCCR-1H cells, total RNAs were isolated from HCCR-1H cells obtained in Example 2 according to the procedure of Reference Example 4 and subjected to northern blot according to the procedure of Reference Example 5 using $^{32}$P-labeled random HCCR-1 cDNA probe.

Figure 13:
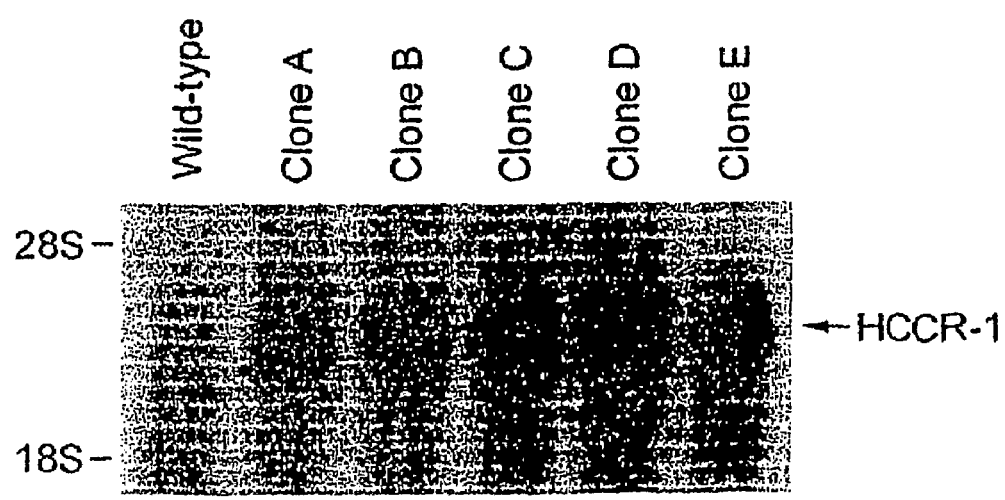
FIG. 13 is the northern blot analysis result showing the expression of HCCR-1 protooncogene in HCCR-1H cells.

FIG. 13 is the northern blot result showing the expression of HCCR-1 protooncogene in HCCR-1H and parental wild-type 293 cells. As can be seen from FIG. 13, about 2.1 kb mRNA single transcript was overexpressed in HCCR-1H cells while not in the parental wild-type 293 cells.

EXAMPLE 13

Tumorigenesis Mechanism Induced by HCCR-1 Protooncogene in Mouse Cells

To examine the tumorigenesis mechanism induced by HCCR-1 protooncogene in mouse cells, abnormalities of protein kinase C (PKC) and telomerase activities, loss of cell cycle checkpoint control, alteration of egr-1, c-fos and GAPDH expression, which have been reported to be relevant to the tumorigenesis process, were assessed as follows.

(Step 1) PKC Activity Assay

Generally, tumors develop secondarily to abnormalities in PKC-mediated signal transduction process. To ensure that HCCR-1 modulates the protein kinase C (PKC) activity, PKC assay was performed using parental wild-type NIH3T3 cells, comparative NIH/3T3 cells transfected with vector pcDNA3 obtained in Comparative Example and HCCR-1M cells obtained in Example 1.

PKC activity was measured using the SigmaTECT™ Protein Kinase C Assay System (Promega) according to the manufacturer's instructions. PKC activity was defined as the difference of the amounts of PKC incorporated into substrate per minute in the absence and presence of phospholipids. Each value is the means ±s.d. of three independent experiments.

Figure 14:
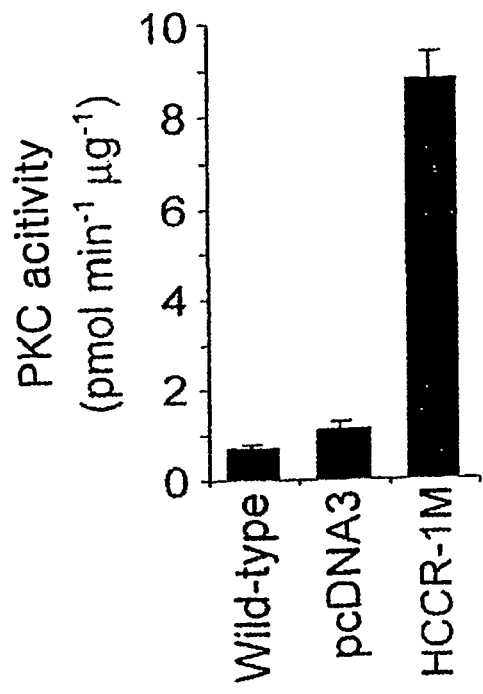
FIG. 14 is a graph showing protein kinase C activities of parental wild-type NIH/3T3 cell, comparative NIH/3T3 cell transfected with vector pcDNA3 and HCCR-1M cell.

FIG. 14 is the graph showing PKC activities of parental wild-type NIH/3T3 cell, comparative NIH/3T3 cell transfected with vector pcDNA3 and HCCR-1M cell. As can be seen from FIG. 14, the PKC activity of HCCR-1M cells is about 10-fold higher than the wild-type. This suggests that HCCR-1 protooncogene enhances the cellular PKC activity.

(Step 2) Telomerase Activity Assay

Based on the report that PKC induces a marked increase in telomerase activity, telomerase activity assay was performed using wild-type NIH/3T3 cells, comparative NIH/3T3 cells transfected with vector pcDNA3 obtained in Comparative Example and HCCR-1M cells obtained in Example 1.

Telomerase activity was measured using the telomerase PCR-ELISA kit (Boehringer Mannheim, USA) according to the manufacturer's instructions. Human telomerase-positive immortalized human kidney cells provided in the kit were used as a positive control. Used as a negative control was the 293 cells pretreated with RNase. Assays were performed with an extract amount equivalent to $1\times10^3$ cells. Results show the average mean optical density (OD) values from four separate experiments (means ±s.d.).

Figure 15:
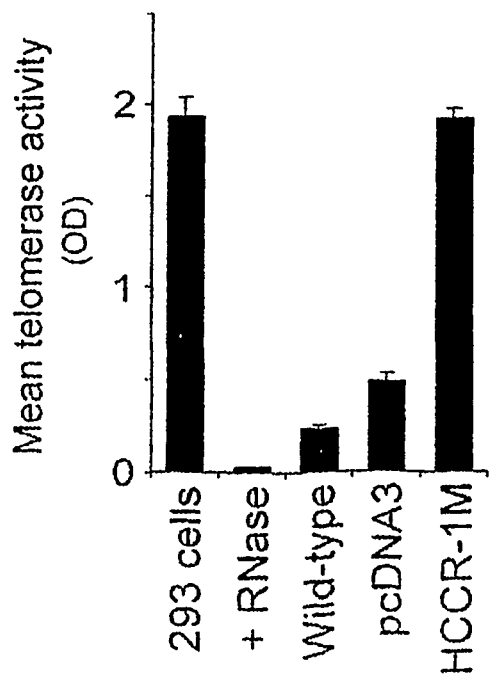
FIG. 15 is a graph showing telomerase activities of positive control 293 cell, negative control cell, parental wild-type NIH/3T3 cell, comparative NIH/3T3 cell transfected with vector pcDNA3 and HCCR-1M cells.

FIG. 15 is the graph showing telomerase activities of positive control cell, negative control cell, parental wild type NIH/3T3 cell, comparative NIH/3T3 cell transfected with vector pcDNA3 and HCCR-1M cells. As can be seen from FIG. 15, the wild-type NIH/3T3 cells showed detectable telomerase activity while HCCR-1M cells have the increased telomerase activity by a factor of about 7 as compared with the parental wild-type cells. The telomerase activity of the positive control cell is high while that of the negative control cells is not detectable. These results are consistent with the previous study (Holt, S. E., Wright, W. E. and Shay J. W. *Mol. Cell Biol.* 16, 2932-2939 (1996)), suggesting that HCCR-1M cell has high telomerase activity induced by activated PKC.

(Step 3) Cell Cycle Test

Tumor cells typically have acquired damage to genes that directly regulate their cell cycles. In order to examine whether there was an alternation in growth properties of HCCR-1M cells, the cell cycle profiles was determined as follows.

HCCR-1M and parental wild-type NIH/3T3 cells cultured at mid-log phase were growth arrested by incubation in a DMEM medium containing 0.5% fetal calf serum for 36 hours. Cells were treated with trypsin, harvested and fixed in 70% ethanol. 50 µg/ml of a propidium iodide staining solution (Sigma) and 100 units per ml of RNase A (Boerhinger Mannheim) were added to $2\times10^6$ cells. After incubation for 30 min., the cellular DNA content was determined by fluorescence analysis at 488 nm using a FACS Caliber (Becton Dickinson). A minimum of $1\times10^4$ cells per sample was analyzed with Modfit 5.2 software.

Percentage of parental wild-type NIH/3T3 and HCCR-1 cells in $G_0/G_1$, S and $G_2/M$ phases were determined and the results are shown in Table I.

TABLE I

| | Wild-type NIH/3T3 | | | HCCR-1M | | |
|---|---|---|---|---|---|---|
| | $G_0/C_1$ | S | $G_2/M$ | $G_0/G_1$ | S | $G_2/M$ |
| Cell Percentage | 55.7 | 20.6 | 24 | 46.6 | 31.5 | 22.4 |

As can be seen from Table I, the percentage of wild-type NIH/3T3 and HCCR-1M cells in S-phase was 20.6% and 31.5%, respectively. These results suggest that there was a significant shift of the cell population out of the $G_0/G_1$-phase into the S-phase in HCCR-1M cells.

To assess the serum-dependent cell cycle progression, HCCR-1M and parental wild-type NIH/3T3 cells were cultured in DMEM medium containing 0.5% fetal calf serum for 36 hours to arrest the growth. The cells were transferred into DMEM medium containing 20% fetal calf serum and harvested at indicated times to determine percentage of cells in $G_0/G_1$, S and $G_2/M$ phases. The results are shown in Table II.

TABLE II

| | Cell Percentage | | | | | |
|---|---|---|---|---|---|---|
| | Wild-type NIH/3T3 | | | HCCR-1M | | |
| Time (hour) | $G_0/C_1$ | S | $G_2/M$ | $G_0/G_1$ | S | $G_2/M$ |
| 0 | 77 | 8.0 | 14.9 | 70 | 21.8 | 8.7 |
| 12 | 72.2 | 14.0 | 14.2 | 66.9 | 24.0 | 9.6 |
| 24 | 49.6 | 13.4 | 37.2 | 56.7 | 24.7 | 19.2 |
| 48 | 58.3 | 18.3 | 23.7 | 52.7 | 30.4 | 17.5 |

As can be seen from Table II, the percentage of parental wild-type NIH/3T3 cells in S-phase at 0 hour was 8% while the percentage of HCCR-1M cells in S-phase was 21.8%. These results suggest that constitutive overexpression of HCCR-1 protooncogene allowed for a relative amount of resistance to serum deprivation-induced $G_0/G_1$ arrest. After transferring cells into DMEM medium containing 20% serum to release cells from the growth arrest, there were consistent increases of over 10% in the S-phase populations of HCCR-1M cells as compared to wild-type NIH/3T3 cells. Therefore, overexpression of HCCR-1 protooncogene could deregulate cell growth by shortening the $G_0/G_1$-phase and increasing the S-phase population of cells.

(Step 4) Expression Patterns of egr-1, c-fos and GAPDH

Based on the fact that expression patterns of egr-1, c-fos and GAPDH involve in tumor formation, expression patterns of egr-1, c-fos and GAPDH in HCCR-1M cells obtained in Example 1 were examined as follows.

Growth of HCCR-1M and parental wild-type NIH/3T3 cells in mid-log phase were arrested by incubation in a DMEM medium containing 0.5% fetal calf serum for 36 hours (quiescent period). The cells were transferred into fresh DMEM medium containing 20% fetal calf serum and cultured for 0, 15, 30, 60 and 120 min. to stimulate the growth (mitotic period). Total RNAs were isolated from quiescent and mitotic cells according to the procedure of Reference Example 4 and subjected to northern blot according to the procedure of Reference Example 5 using $^{32}$P-labeled random-primed egr-1, c-fos and GAPDH cDNA probe.

Figure 16A:
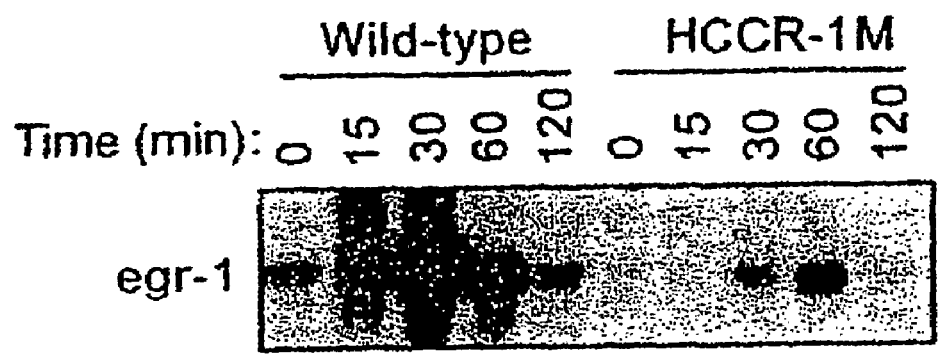
FIGS. 16A to 16C are the northern blot analysis results showing the expression of egr-1, c-fos and glyceraldehyde-2-phosphate dehydrogenase (GAPDH) genes, respectively, in HCCR-1M cell.
Figure 16B:
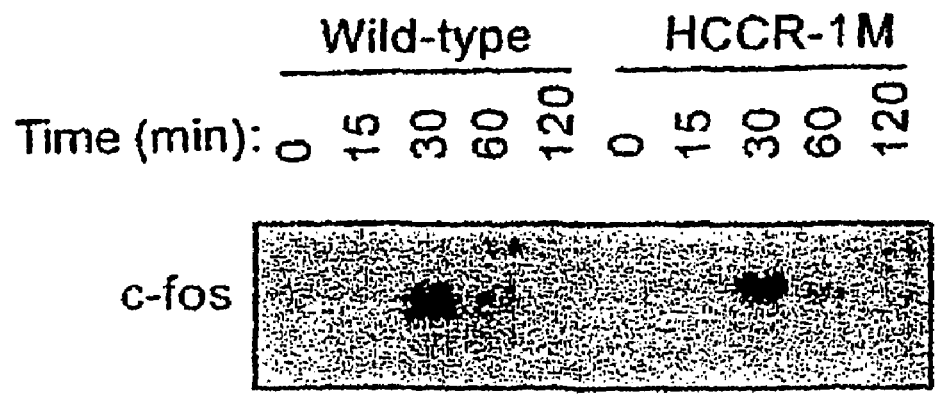
Figure 16C:
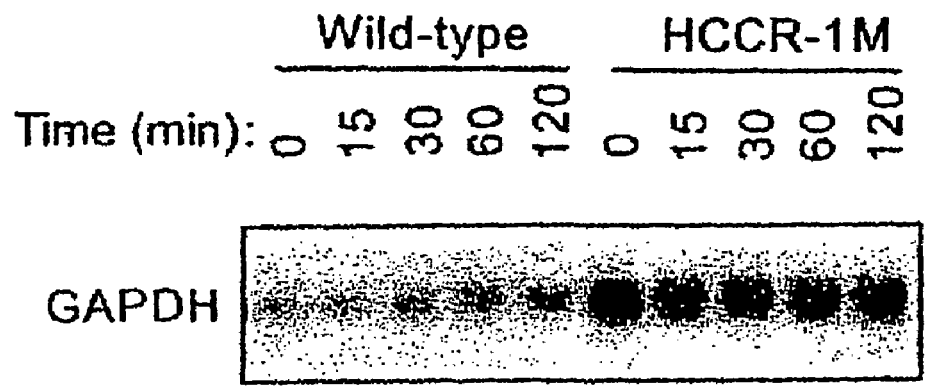

FIGS. 16A, 16B and 16C are the northern blot results showing the expression of egr-1, c-fos and GAPDH, respectively, in HCCR-1H and parental wild-type NIH/3T3 cells. As can be seen from FIGS. 16A to 16C, mitotic HCCR-1M cells show a marked down-regulation of egr-1 expression, up-regulation of GAPDH and no significant difference of c-fos expression compared with the wild-type cells.

These results suggest that deregulation of HCCR-1 gene in mouse NIH/3T3 cells may result in the activation of PKC or telomerase, loss of particular cell cycle checkpoint controls, and downregulation of egr-1 expression, thereby predisposing cells to malignant conversion.

EXAMPLE 14

Tumorigenesis Mechanism Induced by HCCR-1 Protooncogene in Human Cell

To examine the tumorigenesis mechanism induced by HCCR-1 protooncogene in a human cell, expression patterns of p53 tumor suppressor, MDM2, Bax, p21WAF1, p16INK4A and p14$^{ARF}$ genes, which have been reported to be relevant to the tumor, were tested as follows.

(Step 1) Expression Pattern of p53 Tumor Suppressor

In order to examine the expression pattern of p53 in HCCR-1H cell, western and northern blot analyses were conducted as follows.

HCCR-1H cells obtained in Example 2 and parental wild-type 293 cells were lysed and the lysates were subjected to western blot using monoclonal anti-p53 antibody DO-7 (amino acids 37 to 45; Novocastra Laboratories, Ltd., UK) which reacts with wild-type p53 alone; or Ab-5 (Clone DO-7) (amino acids 37 to 45; NEOMARKERS, INC., CA) which reacts with wild-type and mutant p53, according to the procedure of Reference Example 2. The same blot was reacted with anti-human mouse β-actin antibody (Sigma) to confirm total protein content.

Figure 17A:
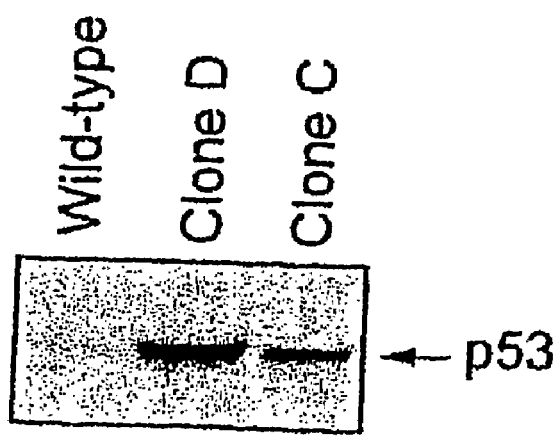
FIG. 17A is the western blot analysis result showing the expression of p53 tumor suppressor gene in HCCR-1H cell.
Figure 17B:
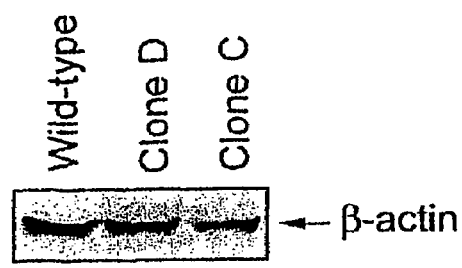
FIG. 17B, β-actin of the same blot.

FIG. 17A is the western blot showing the expression of p53 tumor suppressor in HCCR-1H and parental wild-type 293 cells; and FIG. 17B is the western blot showing β-actin of the same blot. As can be seen from 17A, p53 protein levels were markedly elevated in HCCR-1H cells as compared with the parental wild-type 293 cells.

Further, HCCR-1H cells obtained in Example 2 were cultured in methionine-free RPMI 1640 medium containing 2% fetal calf serum and 2 mM glutamine (Sigma) for 2 hours and then labeled with 100 μl of L-$^{35}$S methionine (Amersham). The cells were washed with 1×Hanks buffer (Gibco, USA), and then further cultured in normal RPMI 1640 medium containing L-methionine for 0.5, 1, 2 or 4 hours. The cells were dissolved in an immunoprecipitation solution (50 mM Tris[pH8.0], 5 mM EDTA, 150 mM NaCl, 1% NP-40, 1 mM phenylmethylsulfonyl fluoride, 10 mM benzamidine, 1 μg of pepstatin per ml, 10 mM sodium bisulfite), washed with 50 μl of protein A-sepharose solution (Sigma) and then quantified. The cell lysate was subjected to immunoprecipitation (Kessler, S. W., *J. Immunol.*, 115, 1617-1623 (1975)) using anti-p53 antibody followed by SDS-PAGE. The above procedure was repeated using Hep 3B hepatoma cells (ATCC HB-8064), as a control lacking p53 gene.

Figure 18:
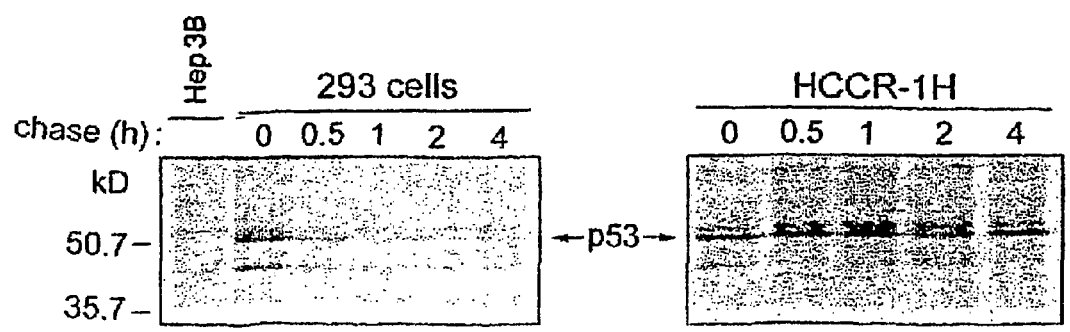
FIG. 18 is the immunoprecipitation result showing the expression of p53 tumor suppressor in HCCR-1H cell.
Figure 19A:
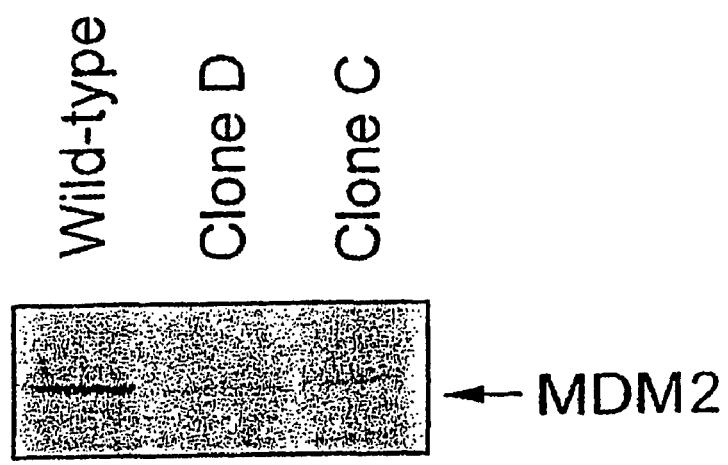
FIGS. 19A, 19C, 19E, 19G and 19I are the western blot analysis results showing the expression of MDM2, Bax, p21WAF1, p16INK4A and p14$^{ARF}$ genes, respectively, in HCCR-1H cell.
Figure 19B:
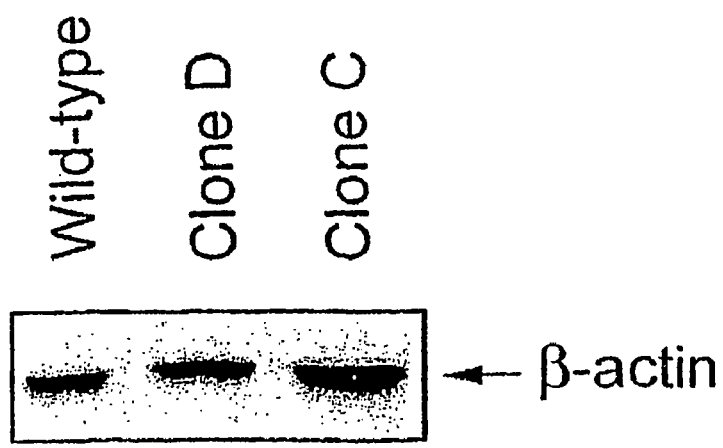
FIGS. 19B, 19D, 19F, 19H and 19J, β-actin in each of the above blots.
Figure 19C:
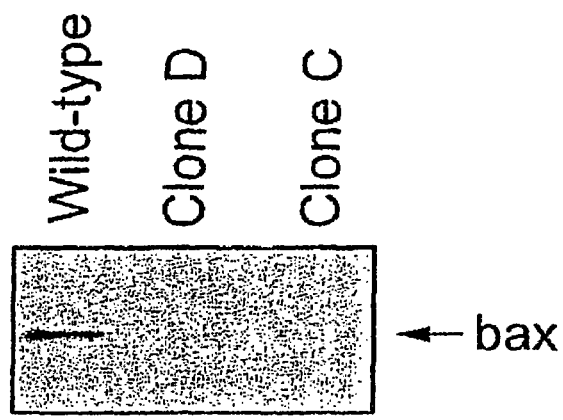
Figure 19D:
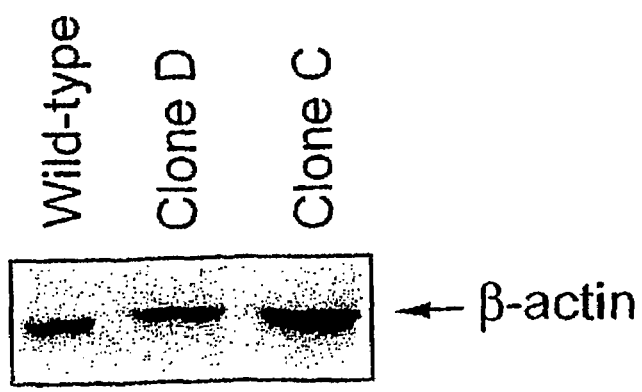
Figure 19E:
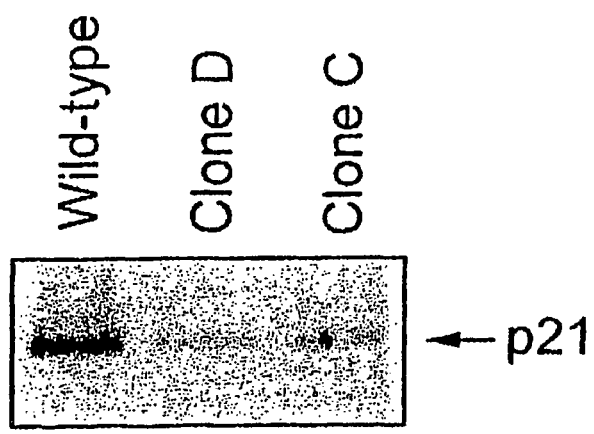
Figure 19F:
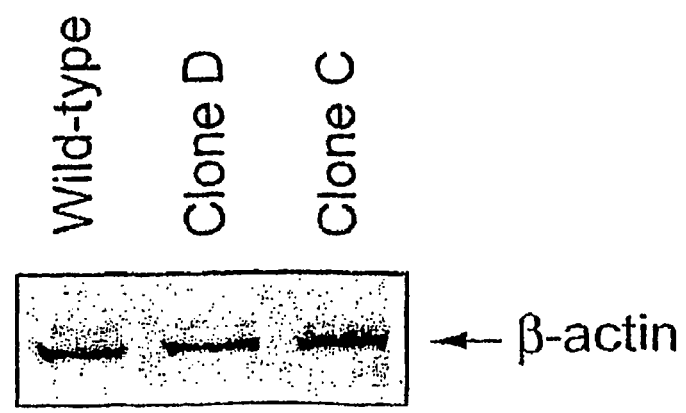
Figure 19G:
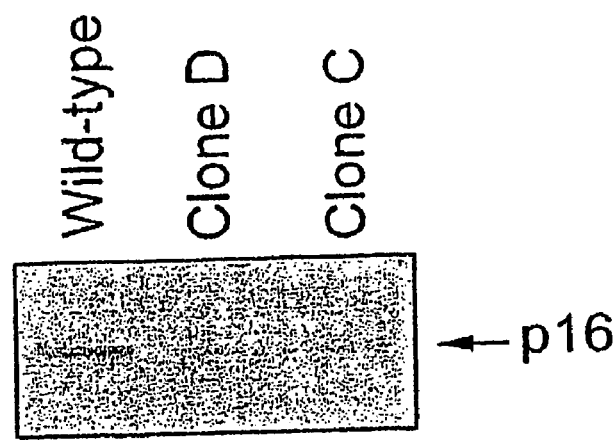
Figure 19H:
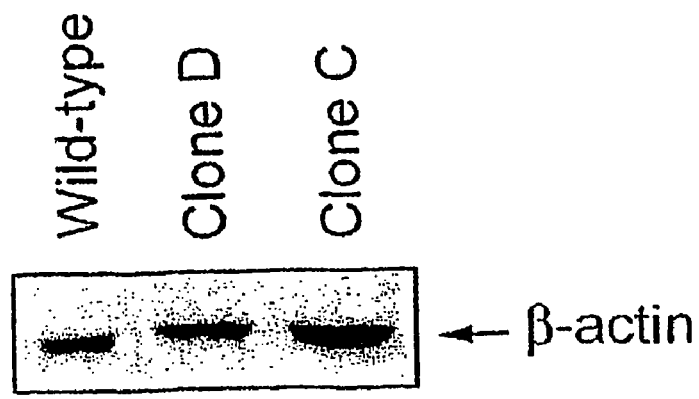
Figure 19I:
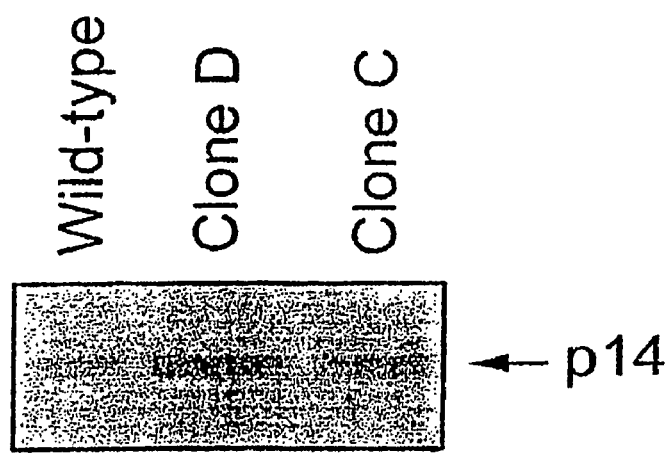
Figure 19J:
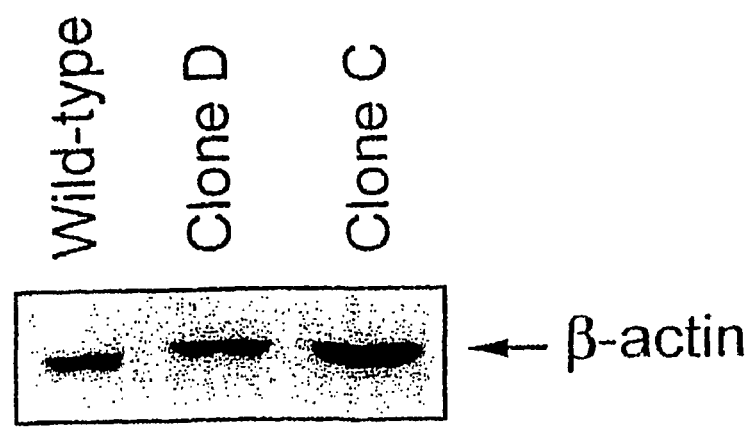

FIG. 18 is the immunoprecipitation result showing the expression of p53 tumor suppressor in HCCR-1H and parental wild-type human 293 cells. As can be seen from FIG. 18, p53 protein levels were markedly elevated in HCCR-1H cells as compared with parental wild-type 293 cells. Therefore, it is believed that in the tumorigenesis mechanism induced by HCCR-1 protooncogene, p53 protein is highly expressed but remains in an inactive form which does not suppress the tumor.

(Step 2) Expression Patterns of MDM2, bax, p21WAF1, p16IN4A and p14$^{ARF}$ Genes Since p53 is a part of a regulatory loop that also involves MDM2, Bax and p14$^{ARF}$, while directly influencing tumor suppressor genes p21WAF1 and p16INK4A, expression patterns of MDM2, Bax, p14$^{ARF}$, p21WAF1 and p16INK4A were assessed.

Using HCCR-1H cells obtained in Example 2; and anti-MDM2, anti-Bax, anti-p21WAF1 and anti p16INK4A antibodies (Oncogene Research Products, USA) and p14$^{ARF}$ (Lab Vision, USA), western blot was conducted according to the procedure of Reference Example 2. The same blot was reacted with anti-β-actin antibody to confirm the total protein content.

FIGS. 19A, 19C, 19E, 19G and 19I are the western blot analysis results showing the expression of MDM2, Bax, p21WAF1, p16INK4A and p14$^{ARF}$, respectively, in HCCR-1H cell; and FIGS. 19B, 19D, 19F, 19H and 19J are β-actin in each of the above blots. As can be seen from FIGS. 19A, 19C, 19E and 19G, MDM2, Bax, p21WAF1, p16INK4A and p14$^{ARF}$ protein levels are decreased compared with the parental wild-type 293 cells. These results suggest that HCCR-1 overexpression may specifically inhibit the transcription of MDM2, Bax, p21WAF1 and p16INK4A, thereby reducing the protein levels thereof.

In summarizing these results together with those of Step 1, it is believed that overexpression of HCCR-1 gene increases p53 stability but the p53 protein does not form an autoregulatory loop which regulates expression of MDM2, bax and p21WAF1 positively. Particularly, as can be seen from FIGS. 19E and 19G, kinase inhibitor protein family p21WAF1 and p16INK4A were downregulated in HCCR-1H cells by a p53-independent mechanism. As can be seen from FIG. 19I, p14$^{ARF}$ did not appear to be aberrantly expressed either in parental wild-type 293 nor in HCCR-1H cells. These results suggest that alteration of the MDM2-p14$^{ARF}$ loop is not a likely mechanism of p53 inactivation.

The above results together with those of Step 3 of Example 13 indicate that the overexpression of HCCR-1 protooncogene both in mouse and human cells can affect cell cycle control and has a correlation with the p53 and p21 cell cycle regulators.

(Step 3) Protein-protein Interaction Partner of HCCR-1

To determine a partner of HCCR-1 in the protein-protein interaction, a yeast two-hybrid screen was conducted as follows.

E. coli JM-109/HCCR1 (KCTC 0667BP) cells were cultured and expression vector pCEV-LAC/HCCR-1 was isolated therefrom. Expression vector pCEV-LAC/HCCR-1 was cleaved with SalI and HCCR-1 protooncogene thus obtained was inserted at BamHI/SalI sites of yeast two-hybrid vector (Clontech, USA) containing pLexA DNA-binding domain to obtain vector pLexA-HCCR-1 expressing a fusion protein of pLexA DNA-binding domain with HCCR-1 protein. Vector pLexA-HCCR-1 was mixed with yeast EGY48 (Clontech, USA) and heated at 42° C. for 10 min. to transform the yeast. The resulting yeast was transformed with human fetal brain cDNA library fused with pB42AD containing pLexA-activating domain (Clontech, USA) in the same method. β-galactosidase filter lift assays were performed by replicaplating the transformant into Trp$^-$, Leu$^-$, His$^-$ selection plates. When a transformant has a partner gene derived from cDNA library, the partner protein fused with pLexA-activating domain binds to HCCR-1 protein fused with pLexA DNA-binding domain to form a blue colony on a plate medium containing X-gal. To eliminate false positives, yeast mating assay (Guarente, L., *Proc. Natl. Acad. Sci. USA*, 90, 1639-1641 (1993)) was conducted.

From the clones thus obtained, a gene encoding a protein-protein interaction partner of HCCR-1 was screened.

The colony thus obtained was cultured in glucose medium and vector containing the partner gene was extracted therefrom using glass beads. The vector was introduced into *E. coli* KC8 (Clontech, USA) by electroporation and the resulting *E. coli* KC8 cells were plated on M9 minimal medium to select a transformant. Plasmid DNA was extracted from the transformant and *E. coli* DH5α was transformed with the plasmid DNA and cultured in LB medium to amplify the plasmid DNA. Plasmid DNA was extracted from the culture and cleaved with HindIII to obtain 1 kb fragment containing the partner gene. The nucleotide sequence of the partner gene was determined to identify TPD52L2 gene (GenBank accession number NM003288). D52 protein encoded by TPD52L2 gene was originally identified through its elevated expression level in human breast carcinoma, and play roles in calcium-mediated signal transduction and cell proliferation (Byrne, J. A., et al., *Cancer Res.*, 55, 2896-2903 (1995); and Byrne, J. A., et al., *Oncogene*, 16, 873-881 (1998)).

(Step 4) Co-transfection

In order to examine interaction of HCCR-1 and D52 proteins, co-transfection was conducted as follows.

E. coli JM-109/HCCR1 (KCTC 0667BP) cells were cultured and expression vector pCEV-LAC/HCCR-1 was isolated therefrom. Expression vector pCEV-LAC/HCCR-1 was cleaved with SalI and the full length HCCR-1 cDNA thus obtained was inserted at SalI site of expression vector N-terminal pFALG-CMV (Sigma, USA) to obtain expression vector pFLAG-HCCR-1 expressing a fusion protein of FLAG with HCCR-1. TPD52L2 gene obtained in Step 3 was inserted at NotI site of expression vector pcDNA3 (Invitrogen, USA) to obtain expression vector pGST-TPD52L2 expressing a fusion protein of GST with D52.

CHO cell was co-transfected with expression vectors pFLAG-HCCR-1 and pGST-TPD52L2 and then cultured in RPMI 1640 medium. After 48 hours, the CHO cells were treated with trypsin and harvested. The CHO cells were washed with PBS and then resuspended in IP buffer (10 mM Tris-HCl [pH 7.4], 150 mM NaCl, 1% NP40, 2 mM sodium vanadate, 10 mM sodium fluoride, 10 mM sodium pyrophosphate, 5 mM EDTA, 10 μg/ml aprotinine, 10 μg/ml leupeptine, 10 μg/ml pepstatine, 1 mM phemylmethylsulfonyl fluoride). The cell suspension was then passed through a 27-gauge needle and the resulting cell lysate was spun to pellet the unbroken cells. The supernatant was precleared by mixing with preimmune IgG and protein A beads (Sigma, USA). FLAG-HCCR-1 or GST-TPD52L2 fusion protein in the cell lysate was immunoprecipitated using anti-FLAG or anti-GST antibody (Sigma, USA) (Kesler, S. W., *J. Immunol.*, 115, 1617-1623 (1975)). The residual protein samples were subjected to western blot using anti-GST or anti-FLAG antibody according to the procedure of Reference Example 2.

Figure 20A:
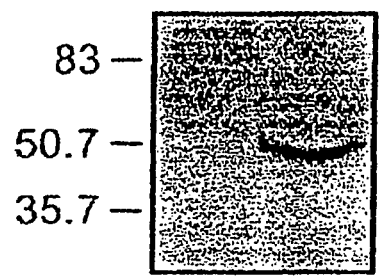
FIG. 20A is the western blot analysis result showing GST protein in the precipitate prepared by immunoprecipitating the FLAG protein of the CHO cell cotransfected with the vector expressing the fusion protein of FLAG and HCCR-1 and the vector expressing the fusion protein of GST and D52.
Figure 20B:
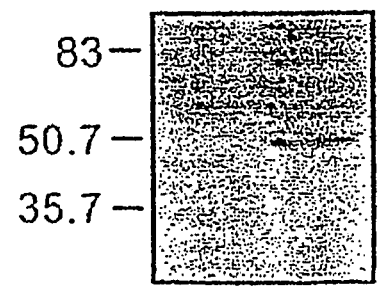
FIG. 20B, PLAG protein in the precipitate prepared by immunoprecipitating the GST protein.

FIGS. 20A and 20B are the western blot analysis results showing GST protein and PLAG protein, respectively. As can be seen from FIGS. 20A and 20B, the fusion protein was detected in both precipitates. These results suggest that D52 protein interacts with HCCR-1 protein.

EXAMPLE 15

Preparation of Transgenic Mouse

In order to ensure that the HCCR-1 protooncogene induce tumorigenesis in vivo, a transgenic mouse expressing HCCR-1 protooncogene under the CMV promoter.

Figure 21:
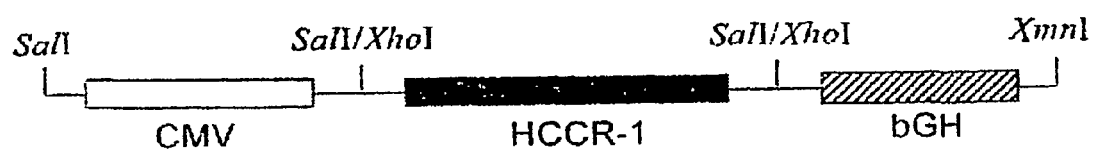
FIG. 21 is a schematic diagram of the nucleic acid construct containing HCCR-1 protooncogene.

To obtain HCCR-1 cDNA useful in the preparation of a transgenic mouse, *E. coli* JM-109/HCCR1 cells (KCTC 0667BP) were cultured and expression vector pCEV-LAC/HCCR-1 was isolated therefrom. Expression vector pCEV-LAC/HCCR-1 was cleaved with SalI and the full length HCCR-1 cDNA thus obtained was inserted at XhoI site of expression vector pcDNA3 to obtain expression vector pcDNA3-HCCR-1. Expression vector pDNA3-HCCR-1 was cleaved with SalI and XmnI, electrophoresed on 0.7% agarose gel, and isolated by electroelution. The isolated DNA fragment was dialyzed against 10 mM Tris-HCl (pH 7.4)/0.2 mM EDTA solution and adjusted to a final concentration of 4 ng/ml. The structure of the resulting DNA contains CMV promoter, HCCR-1 cDNA gene and bovine growth hormone (bGH) polyA sequence as shown in FIG. 21.

The DNA was microinjected into a zygote of mouse FVB/N strain (Samyuk Corp., CAMTAKO, Korea) according to pronuclear DNA microinjection method (Gordon, J. W., et al., *Pro. Natl. Acad. Sci. USA*, 77, 7382-7384 (1980)): The DNA solution was microinjected into the pronucleus of 1-cell stage zygote and the resulting zygote was incubated for 20 hours to select the 2-cell stage embryo. The 2-cell stage embryo was implanted into oviduct of pseudopregnant, recipient ICR mouse (Samyuk Corp., CAMTAKO, Korea). The progeny mice were obtained from the recipient mouse, and DNA samples obtained by tail biopsy of the progeny mice were subjected to southern blot analysis.

Figure 22:
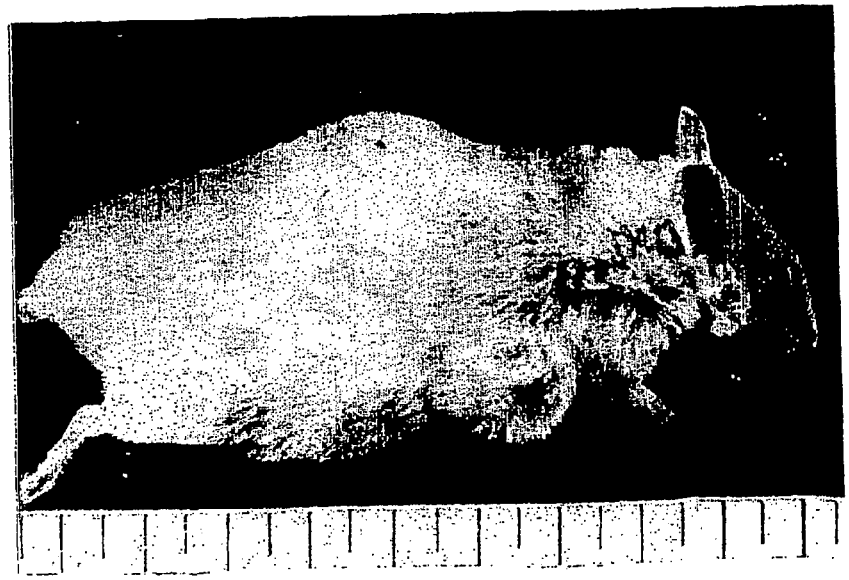
FIG. 22 is a transgenic cancered mouse derived from an embryo having introduced HCCR-1 protooncogene.

FIG. 22 is the transgenic mouse derived from the embryo introduced with HCCR-1 protooncogene. As can be seen from FIG. 22, the tumor mass, measuring about 1.5 cm×1.5 cm, is noted in the right axillary area adjacent to the breast.

The tumor was isolated and observed with the naked eye.

Figure 23:
FIG. 23 is a photograph of breast tumor of the transgenic mouse derived from the embryo carrying introduced HCCR-1 protooncogene.

FIG. 23 is the photograph of the breast tumor of transgenic mouse. As can be seen from FIG. 23, the tumor of transgenic mouse is single, well-circumscribed nodule without capsule.

Figure 24:
FIG. 24 is the hematoxylin-eosin staining result of the breast tumor taken from a transgenic mouse derived from the embryo carrying introduced HCCR-1 protooncogene.

To examine the morphological features of the tumor, the tumor was stained with hematoxylin-eosin. FIG. 24 is the hematoxylin-eosin staining result of the tumor. As can be seen from FIG. 24, the tumor consists of papillary structures and glandular or duck-like structures. Extensive necrosis is noted in the central portion. Normal breast tissue is evident adjacent to the tumor. Cuboid or ovoid cells have indistinct border and a moderate amount of granular, eosinophilic cytoplasm. The tumor cells have an large, pleomorphic and hyperchromatic nuclei and many mitoses, including some atypical forms. Small but distinct nucleoli are noted. These results suggest that the tumor of transgenic mouse exhibits characteristics of ductal papillary adenocarcinoma of breast.

Figure 25:
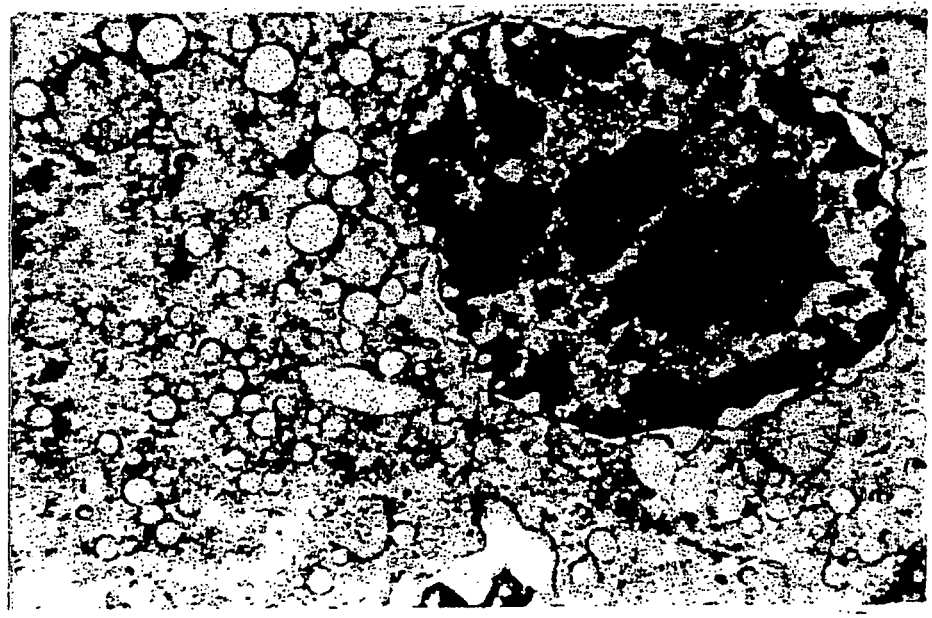
FIG. 25 is a transmission electron microscope picture of the breast tumor taken from the transgenic mouse derived from the embryo carrying introduced HCCR-1 protooncogene.

FIG. 25 is the transmission electron microscope picture of the tumor, wherein the scale bar represents the length of 2 μm. As can be seen from FIG. 25, ovoid tumor cells have abundant cytoplasmic organelles. Nuclei have clumping and margination of chromatin and distinct nucleoli. Cytoplasm is filled with some mitochondria and many vesiculated rER. Some desmosomes are evident.

The embryo of the transgenic mouse was designated HCCR-1, which was deposited on Dec. 26, 2000 with the Korean Collection for Type Cultures under the accession number of KCTC 0924BP.

EXAMPLE 16

Expression of HCCR-1 Protooncogene in Breast, Kidney, Ovary and Stomach Tumor Tissues To examine the expression of HCCR-1 protooncogene in breast, kidney, ovary and stomach tumor tissues, total RNA was isolated from the breast, kidney, ovary and stomach tumor tissues according to the procedure of Reference Example 4 and subjected to northern blot analysis according to the procedure of Reference Example 5 using $^{32}$P-labeled random HCCR-1 cDNA probe. For the comparison, the above procedures were repeated using normal breast, kidney, ovary and stomach tissues.

Figure 26A:
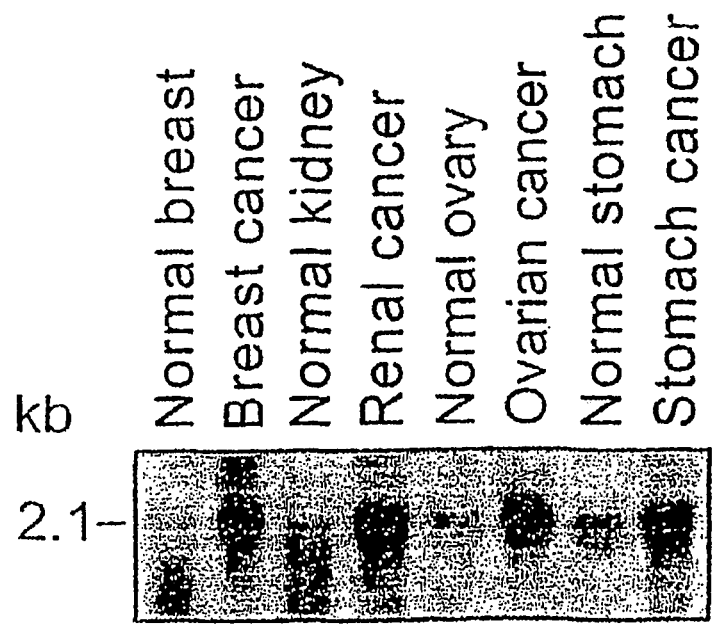
FIG. 26A is the northern blot analysis result showing the expression of HCCR-1 protooncogene in breast, kidney, ovary and stomach tumor tissues.
Figure 26B:
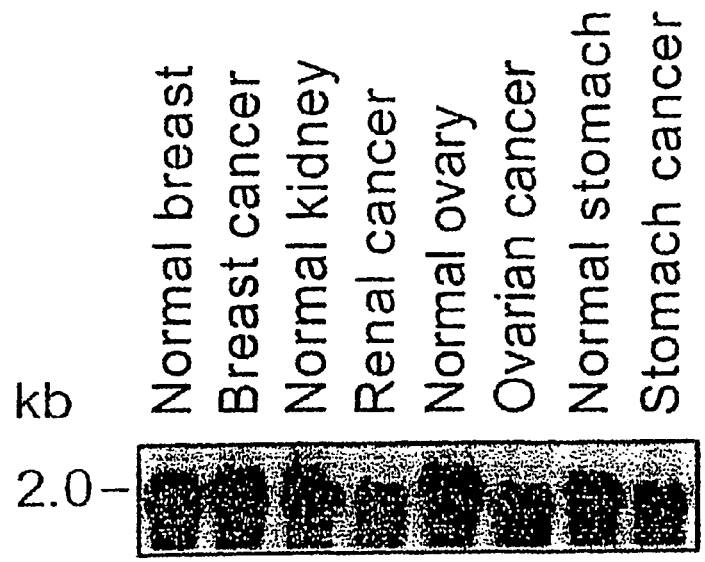
FIG. 26B, the same blot hybridized with β-actin probe.

FIG. 26A is the northern blot analysis result showing the expression of HCCR-1 protooncogene in breast, kidney, ovary and stomach tumor tissues; and FIG. 26B is the same blot hybridized with β-actin probe. As can be seen from FIGS. 26A and 26D, the human breast, kidney, ovary and stomach tumor tissues showed increased expression of HCCR-1 protooncogene when compared with the normal tissues.

To examine the HCCR-1 protein expressed in the breast, kidney, ovary and stomach tumor tissues, the breast, kidney, ovary and stomach tumor tissues were subjected to western blot analysis using anti-HCCR-1 serum obtained in Preparation Example 2 according to the procedure of Reference Example 2.

Figure 27:
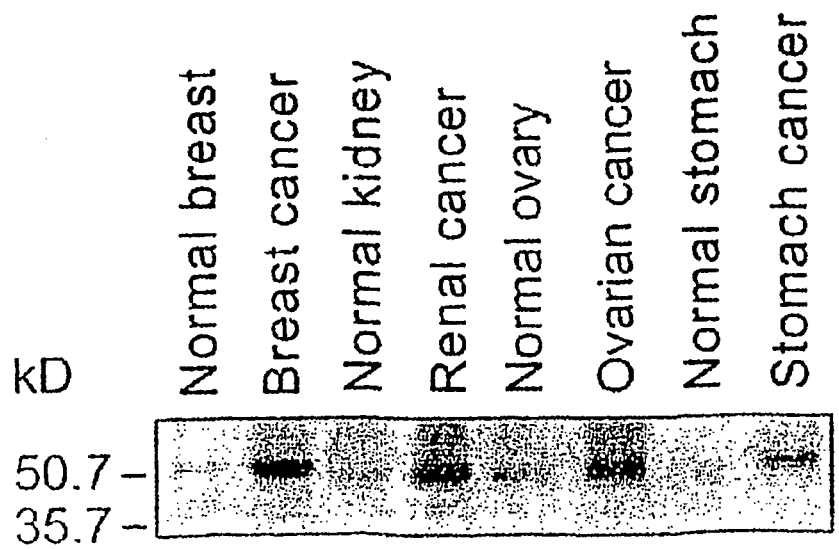
FIG. 27 is the western blot analysis result showing the expression of HCCR-1 protooncogene in human breast, kidney, ovary and stomach tumor tissues.

FIG. 27 is the western blot analysis result showing the expression of HCCR-1 protooncogene in human breast, kidney, ovary and stomach cancer tissues. As can be seen from FIG. 27, the human breast, kidney, ovary and stomach tumor tissues showed increased expression of 50 kDa HCCR-1 protein expression when compared with their normal counterparts, respectively.

EXAMPLE 17

Chromosomal Localization of HCCR-1 Protooncogene

The full length HCCR-1 cDNA obtained in Preparation Example 1 was labeled using random prime labeling kit (Promega, USA) to obtain a probe. Human placenta Lambda Genomic Library (Stratagene, USA) was screened using the probe to obtain 20 kb genomic DNA.

The genomic DNA was subjected to fluorescence in situ hybridization (FISH) (Cherif, D., et al., *Proc. Natl. Acad. Sci. USA*, 87, 6639-6649 (1990)): The genomic DNA on a slide was labeled with SpectrumRed-dUTP using nick translation kit (Vysis, USA). The slide was observed under a Zeiss fluorescence microscope. Chromosomes were counterstained with DAPI (Sigma, USA).

Figure 28:
FIG. 28 is the fluorescence in situ hybridization analysis result showing the position of HCCR-1 protooncogene on the human chromosome.

FIG. 28 is the fluorescence in situ hybridization analysis result showing that HCCR-1 protooncogene is located on long arm (12q) of 12th chromosome.

While the subject invention has been described and illustrated with reference to the preferred embodiments only, it may be apparent to those skilled in the art that various changes and modifications can be made therein without departing from the spirit and scope of the present invention which is defined in the appended claims.

What is claimed is :

1. An isolated mammalian cell transformed with an expression vector comprising a human protooncogene which has a nucleotide sequence of SEQ ID NO: 1.

2. The isolated mammalian cell of claim 1, which is mouse cell line HCCR-1M(KCTC 0923BP) or human cell line HCCR-1H(KCTC 0922BP).

3. A mouse embryo whose genome carries an introduced nucleic acid construct comprising a human protooncogen which has the nucleotide sequence of SEQ ID NO: 1.

4. The mouse embryo of claim 3, wherein the mouse is FVB/N strain.

5. The mouse embryo of claim 4, which is mouse embryo HCCR-1(KCTC 0924BP).

6. A transgenic cancer mouse derived from the embryo of claim 3.

7. The transgenic mouse of claim 6, wherein the cancer is ductal papillary adenocarcinoma of breast.

8. A transgenic cancer mouse derived from the embryo of claim 4.

9. A transgenic cancer mouse derived from the embryo of claim 5.

* * * * *